United States Patent [19]

Calvet et al.

[11] Patent Number: 5,082,937
[45] Date of Patent: Jan. 21, 1992

[54] BENZODIAZEPINES AND APPLICATIONS IN THERAPEUTIC PRACTICE

[75] Inventors: Alain P. Calvet, L'Hay Les Roses; Jean-Louis Junien, Sevres; Yves R. Pascal, Rueil Malmaison; Xavier B. Pascaud, Paris; Francois J. Roman, Vitry Sur Seine, all of France

[73] Assignee: Jouveinal S.A., Paris, France

[21] Appl. No.: 584,150

[22] Filed: Sep. 18, 1990

[30] Foreign Application Priority Data

Sep. 28, 1989 [FR] France ............... 89 12700

[51] Int. Cl.⁵ .................. A61K 31/55; C07D 471/06; C07G 487/06
[52] U.S. Cl. .................................. 540/496
[58] Field of Search ........................ 540/496

[56] References Cited

U.S. PATENT DOCUMENTS 4,929,614  5/1990  Calvet et al. ............. 540/496

Primary Examiner—Robert T. Bond
Attorney, Agent, or Firm—Cushman, Darby & Cushman

[57] ABSTRACT

Benzodiazepines of formula

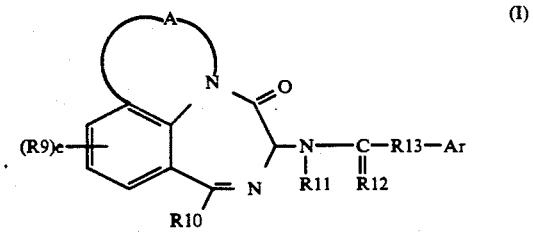

(I)

in which
$R^9$ is hydrogen or chlorine, R10 is phenyl, possibly substituted, R11 is hydrogen, R12 is oxygen or sulphur, R13 is an NH group, Ar is aromatic or heteroaromatic comprising one or more rings and in which, in particular, A is an ethylene or trimethylene bridge; e is 1 or 2; which are gastrin antagonists and/or central antagonists of cholecystokinin.

22 Claims, No Drawings

BENZODIAZEPINES AND APPLICATIONS IN THERAPEUTIC PRACTICE

The present invention relates to benzodiazepines, their process of production, intermediate products and applications in therapeutic practice.

Cholecystokinin, abbreviated below to CCK, is a peptide comprising thirty three amino acids as initially isolated, but it circulates in the organism active forms comprising thirty nine, twelve and eight amino acids. The form comprising the eight amino acids at the carboxylic acid termination of the peptide is the shortest amino acid chain exhibiting activity. It is designated below by the abbreviations CCK-8, CCK-8 SO4 or sulphated CCK-8; these latter two abbreviations signify that the phenol group of the tyrosine in position 27 of the cholescystokinin has been esterified by a —SO3H group, as is the case in the natural form. Biochemical studies have revealed the existence of two types of cholescystokinin receptors in the mammalian organism, the first being designated below receptor CCK A exhibiting a preferred peripheral localization and the second designated below CCK B exhibiting a preferred central localization. Furthermore, gastrin, which is a hormone involved in regulation of the gastro-intestinal system, has structural similarities with cholecystokinin.

European patent application No. 88302141.2, submitted by the firm Merck & Company, describes benzodiazepines having the following formula:

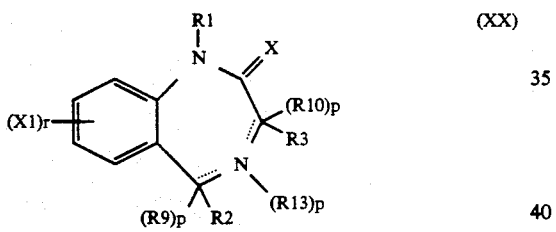

designated formula (XX) in the present memorandum, in which:

R1 is hydrogen, linear or branched lower alkyl, lower alkenyl, lower alkynyl, —X12—COOR6, —X11-lower cycloalkyl, —X12—nR4R5, —X12—C-(O)—NR4R5, —X12—CN or X11—C(X10)3

R2 is hydrogen; phenyl possibly substituted by one or more groups selected from among halogen, lower alkyl, lower alkyloxy, lower alkylthio, carboxyl, lower alkyloxycarbonyl, nitro, trifluoromethyl or hydroxy; 2-, 3-, 4-pyridyl;

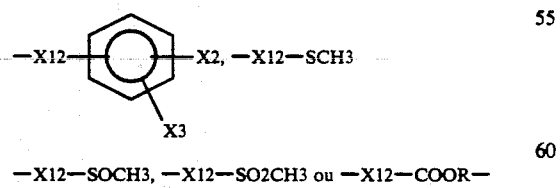

—X12—SOCH3, —X12—SO2CH3 ou —X12—COOR—

R3 is —X11NR18(CH2)qR16, —X11NR18C-(=O)X11R7, —NH(CH2)3NHR7, —NH(CH2)3NH-COR7, —X11C(=O)X9X11R7, —X11X9C-(=O)C(CH6CH2R7)—NHCOOR14, —X11NR18C-(=O)—X9aX11R7, —X11X9C(=O)—CH(NH-2)—CH2R7,

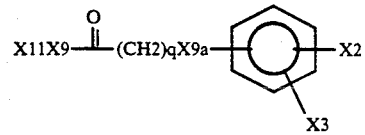

—X11NR12SO2(CH2)qR7 or —X11C(=O)R7, subject to the fact that R10 is neither hydrogen nor methyl when R3 is —X11COR7.

R4 and R5 are independently equal to R6 or form with the nitrogen atom of the NR4R5 group a heterocycle of 4 to 7 chain links unsubstituted or mono or disubstituted, saturated or unsaturated; a heterocycle of 4 to 7 chain lines condensed with a benzene ring or one of the two systems described below comprising in addition a second heteroatom selected between O and NCH3 and the substituent or substituents of which are lower alkyls, R6 is hydrogen, alkyl or lower cycloalkyl, phenyl possibly substituted or lower phenyl-alkyl possibly substituted, the substituents on the phenyl or lower phenyl-alkyl being possibly 1 or 2 in number and selected between halogen, lower alkyl, lower alkyloxy, nitro or trifluoromethyl, R7 is α- or β-naphthyl; phenyl possibly mono or disubstituted by halogen, nitro, hydroxy, —X11NR4R5, lower alkyl, CF3, CN, SCF3, CH=CH, CH2SCH3, OC(=O)CH3, OCHF2, SH, SPh, PO3H, lower alkyloxy, lower alkylthio or COOH; 2-, 3-, 4-pyridyl,

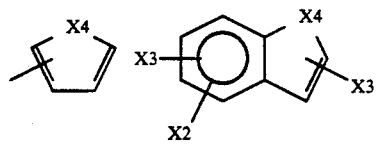

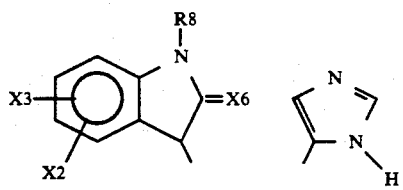

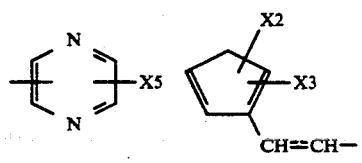

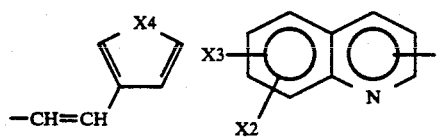

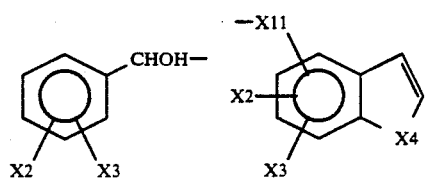

R8 is hydrogen, lower alkyl, lower cycloalkyl, —X-12CONH2, —X12COOR6, —X12-lower cycloalkyl, —X12NR4R5, —COCH(NH2)—CH2R12, —C—=O)—CH (CH2R12)—NHCOOR11,

[structure: —X12— phenyl with X2, X3 substituents]

[structure: X3—phenyl(X2)—(CH2)qC(=O)—X11—]

R9 and R10 are independently H, OG or CH3.
R11 and R12 are independently lower alkyl or lower cycloalkyl,
R13 is H, O, lower alkyl, lower cycloalkyl or acyl,
R14 is lower alkyl or lower phenylalkyl,
R15 if H, —NH2, lower alkyl or

[structure: phenyl with X2, X3 substituents]

R16 is α- or β-naphthyl or 2-indolyl, R18 is H or lower alkyl,
p is zero when the adjacent optional double bond is unsaturated and one when it is saturated except where R13 is O, in which case p=1 and the adjacent optional double bond is unsaturated,
q is 1-4,
r is 1 or 2,
X1 is H, —NO2, CF3, CN, OH, halogen, lower alkyl, lower alkoxy, lower alkylthio, —X11COOR6 or —X11NR4R5.
X2 and X3 are independently H, —NO2, OH, halogen, lower alkyl, lower alkoxy, lower alkylthio,
X4 is X, O, CH2 or NR8,
X5 is H, CF3, CN, —COOR6, —NO2 or halogen,
X6 is O or HH,
X7 is O, S, HH or NR15 subject to the fact that X7 can only be NR15 when R1 is not H,
X8 is H or lower alkyl,
X 9 and X9a are independently NR18 or O,
X10 is F, Cl or Br,
X11 is absent or linear or branched alkylidene comprising 1 to 4 carbon atoms,
X12 is linear or branched alkylidene comprising 1 to 4 carbon atoms, subject to the fact that where (X1)r is chlorine in position 7, R1 is H and R2 is unsubstituted phenyl where R3 is not NHC(O)—(CH2-)2—C6H5 or NHC(O)—C6H5.

Furthermore, the preparation and pharmacological properties of these benzodiazepines have been published in references in the articles listed below:
J. Med. Chem. 1989, 32, 13–16
J. Med. Chem. 1988, 31, 2235–2246
European Journal of Pharmacology 162 (1989) 273–280

These publications bring out in particular the existence of an enantiomer compound of formula (XXa)

[structure (XXa)]

for which a selective affinity both for the B receptors of cholecystokinin and for the gastrin receptors in relation to the A receptors of cholecystokinin has been demonstrated "in vitro". The results presented show that the CCK-A/gastrin activity ratio is 290/1.9 or about 150 times more favourable to the activity of the compound on the gastrin receptors. The Applicant has reproduced these experiments and found a ratio of 1419/4.7 or about 300 times more favourable to activity on the gastrin receptors.

In addition to the European patent application No. 89116504.5, submitted by the company Fujisawa on 07.09.89 and subsequently published on the date of priority applicable to the present Application, tricyclic compounds having an antagonist activity in relation to cholecystokinin (CCK) have been described without further details of their specificity of action on the receptors described above.

[structure with X, A, N, O, NH—R2, R1]

in which,
R1 is aryl, possibly substituted
X represents —O— or —CH(R3)— in which R3 is hydrogen or lower alkyl,
A is a valence bond or lower alkylene which may comprise one or more loweralkyl groups,
R2 is hydrogen or an acyl group.

Benzodiazepines have moreover now been found which, in the racemic form, exhibit simultaneously an activity comparable to or better than that of the prior art on the gastrin receptors and/or on the B receptors of cholecystokinin and have in the case of certain compounds an appreciably lower activity on the A receptors of cholecystokinin. This property permits the utilization of the products of the invention in the treatment of diseases linked with the central cholecystokinin receptor or the gastrin receptor with little of no secondary effect on systems linked with the cholecystokinin peripheral receptor, in mammals and in particular in man. This means, in particular, that the benzodiazepines of the invention are capable of inhibiting gastric secretion without inducing increased gastric evacuation as a side effect. The products of the invention may therefore be useful in the treatment of pain, hyperplasia of the pancrease or colon, Zollinger-Ellison's syndrome, gastroduodenal ulcers and in more general terms phenomena controlled by gastrin, in particular digestive motricity.

The object of the invention is accordingly benzodiazepines of formula (I):

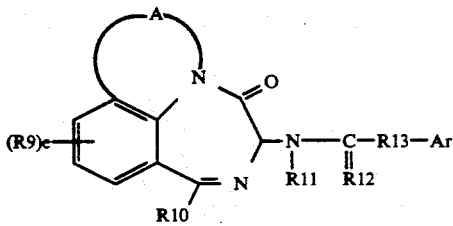

in which,
R9 is hydrogen, nitro, halogen, cyano, trifluoromethyl, hydroxy, lower alkyl, lower alkoxy, —COOR20, —N(R21)—R22,
R10 is phenyl, possibly mono to trisubstituted with identical or different groups chosen from among halogen, lower alkyl, lower alkoxy, cyano, nitro or trifluoromethyl;
R11 is hydrogen or lower alkyl;
R12 is an oxygen atom or a sulphur atom;
R13 is a —N(R24)— group;
R20 is hydrogen or lower alkyl;
R21 and R22 are identical or different and may be hydrogen or a lower alkyl group;
R24 is hydrogen or lower alkyl;
Ar is an aromatic hydrogen group or heteroaromatic group, comprising one or two condensed ring, each of the rings comprising 5 to 7 atoms including zero to two nitrogen heteroatoms; this aromatic or heteroaromatic group being possibly mono or disubstituted with identical or different groups selected from among lower alkyl, carboxyl, lower alkoxy carbonyl, sulphonyl, sulphamoyl, cyano, nitro, trifluoromethyl or, subject to R12 being a sulphur atom, with halogen or lower alkoxy groups;
A is [—CH(R1)—] in which R1 is hydrogen or lower alkyl;
a is two, three or four;
e is one or two.

In the preceding or subsequent arguments:
halogen is understood to mean fluorine, chlorine, bromine or iodine;
pseudohalogen is understood to mean groups which react in similar fashion to halogens, in particular in nucleophilic substitution reactions, or behave like nucleofuse groups. Examples of such groups are methanesulphonate, benzenesulphonate, paratoluenesulphonate and nitride.
lower alkyl is understood to mean linear or branched alkyl groups comprising from one to seven carbon atoms such as: methyl, ethyl, propyl, isopropyl, butyl, isobutyl, tertiobutyl and various isomers of pentyl, hexyl and heptyl groups,
lower alkoxy is understood to mean a (—O—alkyl) group in which the alkyl group is a lower alkyl as defined above,
lower alkoxy carbonyl is understood to mean an (alkyl—O—C(=O)—) group in which the alkyl group is a lower alkyl group as defined above.

The invention comprises the benzodiazepines of formula (I), in both the racemic and also the pure enantiomer form.

The invention comprises also the pharmacologically acceptable salts of compounds of formula (I) where these include a basic or acid form.

Pharmacologically acceptable salt of a compound of formula (I) including a basic portion shall be understood to mean the addition salts of compounds of formula (I) formed from nontoxic mineral or organic acids, such as for example the salts of hydrobromic, hydrochloric, sulphuric, sulphamic, phosphoric, nitric, acetic, propionic, succinic, glycolic, stearic, lactic, malic, tartaric, citric, mucic, ascorbic, pamoic, maleic, hydroxymaleic, phenylacetic, glutamic, benzoic, salicylic, sulphanilic, acetoxyenzoic, fumaric, toluene-sulphinic, ethanedisulphonic, oxalic, isothionic, and other acids. The various quaternary ammonium salts of derivatives (I) are also included in this category of compounds of the invention.

Pharmacologically acceptable salt of a compound of formula (I) including an acid portion is understood to mean the usual salts of compounds of formula (I) formed from nontoxic mineral or organic bases such as for example alkaline and alkaline earth (lithium, sodium, potassium, magnesium and calcium) metal hydroxides, amines (dibenzylethylenediamine, trimethylamine, piperidine, pyrrolidine, benzylamine and others) or again quaternary ammonium hydroxides such as tetramethylammonium hydroxide.

Among these new benzodiazepines, preference is given to those in which R12 is a sulphur atom. Preference is also given, where the Ar group comprises a single ring, to a methyl-substituted benzene group and, subject to R12 being sulphur, to a bromine atom-substituted benzene group. Where the Ar group comprises two rings, preference is given to the naphthalene ring and, where Ar comprises two rings one of which is a heterocyclic ring, it should preferably include only one nitrogen atom and in this case particular preference is given to benzodiazepines according to the invention in which the Ar group is quinoline.

Among these new benzodiazepines, preference is given to those in which a is 2 or 3 and in which R1 is hydrogen provided that A is an ethylene (—CH2—CH2—) or trimethylene (—CH2—CH2—CH2—) bridge.

Among the benzodiazepines of the invention, preference is also given to:
those in which R9 is a hydrogen atom or a chlorine atom in the para position in relation to the nitrogen atom which is shared with the diazepine ring and the ring containing group A and those in which e=1,
those in which R10 is a phenyl group, or a phenyl group substituted with a fluorine atom in the ortho position, or with a methyl radical in the para position in relation to the atom linking R10 to the diazepine ring,
those in which R11 is hydrogen,
those in which R13 is N(R24), the preferred R24 group being hydrogen.

The absolute configuration of the carbon in the diazepine ring bearing the substituent —N(R11)—C(=R12)—R13—Ar is important for the selectivity of the benzodiazepine of formula (I) in relation to one or other of the CCK-A, CCK-B receptors or gastrin and preference is given in general to the optical isomers of the benzodiazepines of the invention. In particular, where a compound is required having selectivity for the B receptor of the cholecystokinin, preference is given in general to the isomer in which the asymmetrical carbon atom of the diazepine ring has the absolute configuration (R) according to the nomenclature of Cahn, Ingold and Prelog.

More specifically, the preferred benzodiazepines are:
(4R,S)-N-(keto-3-phenyl-6-tetrahydro-1,2,3,4-pyrrolo[3,2,1-j,k] benzodiazepine-[1,4]-yl-4)-N'-(methyl-3-phenyl-)-urea.
(4R)-N-(keto-3-phenyl-6-tetrahydro-1,2,3,4-pyrrolo[3,2,1-j,k] benzodiazepine-[1,4]-yl-4)-N'-(methyl-3-phenyl-)-urea.
(5R,S)-N-(keto-4-phenyl-7-hexahydro-1,2,3,3a,4,5-pyrido[3,2,1-j,k] benzodiazepine-[1,4]-yl-5)-N'-(methyl-3-phenyl-)-urea,
(5R)-N-(keto-4-phenyl-7-hexahydro-1,2,3,3a,4,5-pyrido[3,2,1-j,k] benzodiazepine-[1,4]-yl-5)-N'-(methyl-3-phenyl-)-urea,
(5R,S)-N-(keto-4-phenyl-7-hexahydro-1,2,3,3a,4,5-pyrido[3,2,1-j,k] benzodiazepine-[1,4]-yl-4)-N'-(nitro-4phenyl-)-urea and its isomers,
(5R,S)-N-(keto-4-phenyl-7-hexahydro-1,2,3,3a,4,5-pyrido[3,2,1-j,k] benzodiazepine-[1,4]-yl-5)-N'-(bromo-4-phenyl-)-thiourea and its isomers,
(5R,S)-N-(keto-4-phenyl-7-hexahydro-1,2,3,3a,4,5-pyrido[3,2,1-j,k] benzodiazepine-[1,4]-yl-5)-N'-(naphthyl-urea and its isomers,
(5R,S)-N-(keto-4-phenyl-7-hexahydro-1,2,3,3a,4,5-pyrido[3,2,1-j,k] benzodiazepine-[1,4]-yl-5)-N'-(quinoleinyl-3)-urea and its isomers.

The invention relates also to a process for the preparation of benzodiazepines of formula (I), a process illustrated in schemes 1 and 2 and which consists
(a) in the case of a benzodiazepine of formula (I) in the racemic form (R,S):

(i) in the case where R11 is hydrogen, R13 is NH and R12 is oxygen, in reacting a racemic amine of formula (II), in which A, R9, R10 and e have the connotation defined above with an arylisocyanate of formula Ar—N=C=O, Ar having the connotation defined above in order to obtain a racemic benzodiazepine of formula (Ia) (Scheme 1);

(ii) in the case where R11 is hydrogen, R13 is N(R24), R24 being lower alkyl and R12 oxygen, in reacting a racemic amine of formula (II), in which A, R9, R10 and e have the connotation defined above with a protective agent of the amines of formula (XII):R25-CH2X, in which R25 is a benzene ring possibly mono, di or trisubstituted with identical or different substituents chosen form among the halogens and X is a halogen or pseudohalogen group having the connotation defined above or again a protective agent (XIIa) R25—CHO operating under reducing amination conditions to obtain the benzylamine of formula (XIX), which is reacted with an arylisocyanate of formula Ar—N=C=O as in paragraph (i) above, in order to obtain the urea of formula (XV).

The urea of formula (XV) thus obtained is alkylated with a reagent of formula (XIV): R24-R39 in which R24 is lower alkyl and R39 is a halogen or a pseudohalogen in order to obtain a tetrasubstituted urea of formula (XVI) then eliminating the protector group R25-CH2 by hydrogenolysis with a reagent selected between sodium in liquid ammonia or hydrogen in the presence of a hydrogenation catalyst such as a metal finely divided on a support such as carbon, in order to obtain a racemic benzodiazepine of formula (Ib) (Scheme 1);

(iii) in the case where R11 is lower alkyl, R13 is NH and R12 is oxygen, in reacting a racemic amine of formula (II), in which A, R9, R10 and e have the connotation defined above, with an alkylation agent for amines of formula (XIII) R11-R36, in which R11 is lower alkyl and R36 is a halogen or pseudohalogen as defined above, or with an aldehyde of formula (XIIIa) R37—CHO, in which R37 is hydrogen or lower alkyl such that (R37—CH2—)=(R11—) and under reducing amination conditions i.e. in the presence of hydrogen and a hydrogenation catalyst (homogeneous or heterogeneous) which is selected from among noble metals or noble metal oxides finely divided and deposited on a finely divided support, soluble complexes of transition metals or in the presence of a reducing agent such as sodium borohydride or preferably sodium cyanoborohydride, in order to obtain an amine of formula (IIa), which is reacted with an arylisocyanate of formula Ar—N=C=O, as in paragraph (i) above) in order to obtain a racemic benzodiazepine of formula (Ic) (Scheme 1);

(iv) in the case where R11 is lower alkyl, R13 is N-R24, R24 being lower alkyl, and R12 is oxygen, in reacting a racemic benzodiazepine of formula (Ic), in which A, R9, R10, R11, Ar and e have the connotation defined above, with an alkylation reagent (XIV) in order to obtain a racemic benzodiazepine of formula (Id) (Scheme 1);

(v) in the case where R11 is hydrogen, R13 is NG and R12 is sulphur, in reacting a racemic amine of formula (II), in which A, R9, R10 and e have the connotation given above, with an arylisothiocyanate of formula Ar—N=C=S, Ar having the connotation given above, in order to obtain a racemic benzodiazepine of formula (Ie) (Scheme 2);

(vi) in the case where R11 is hydrogen, R13 is N(R24), R24 being lower alkyl, and R12 is sulphur, in reacting a racemic benzylamine of formula (XIX), in which a, R9, R10, R25 and e have the connotation given above, with an arylisothiocyanate of formula Ar—N=C=S, in order to obtain the thiourea of formula (XVII), which is reacted with an alkylation reagent (XIV) defined above, in order to obtain a tetrasubstituted thiourea of formula (XVIII), then eliminating the protecting group by hydrogenolysis by reaction with sodium in liquid ammonia, in order to obtain a racemic benzodiazepine of formula (If) (Scheme 2);

(vii) in the case where R11 is lower alkyl, R13 is NH and R12 is sulphur, in reacting a racemic amine of formula (IIa), in which A, R9, R10, R11 and e have the connotation given above, with an arylisothiocyanate of formula Ar—N=C=S, Ar having the connotation given above, in order to obtain a racemic benzodiazepine of formula Ig), (Scheme 2);

(viii) in the case where R11 is lower alkyl, R13 is N-R24, R24 being lower alkyl, and R12 is sulphur, in reacting a racemic benzodiazepine of formula (Ig), in which A, R9, R10, R11, Ar and e have the connotation given above, with an alkylation reagent (XIV) in order to obtain a racemic benzodiazepine of formula (Ih) (Scheme 2);

(b) in the case of a benzodiazepine of formula (I) in the optically active form (R or S form):

In operating with the starting products (II) in the form of appropriate enantiomers in identical fashion to that described in each of the eight previous cases in order to obtain benzodiazepine enantiomers of formula (Ia), (Ib), (Ic), (Id), (Ie), (If), (Ig) or (Ih).

The pharmaceutically acceptable salts of the present invention may be prepared on the basis of compounds of formula (I) by conventional procedures. This preparation consists in general in reacting the reactive function of the benzodiazepine of the invention with a stoichiometric quantity or excess of the appropriate salt-forming reagent in a solvent or solvent mixture.

PREPARATION OF COMPOUNDS OF FORMULA I

The preparation of compounds of formula (I) described below relates indiscriminately to racemic compounds (I) or to their enantiomers based on racemic or optically pure amines of formula (II) or (IIa). The syntheses are summarized in schemes 1 and 2 and set out in detail below. The products obtained after reaction are, if necessary, purified by silica column chromatography (flash chromatography) or by high pressure liquid chromatography (HPLC) followed if necessary by recrystallization.

(i) Preparation of compounds (Ia) and (Ic) (Scheme 1)

In the case where R13 is NH and R12 is an oxygen atom, in particular, the following procedure may be followed: A compound of formula (II) or (IIa) is dissolved in 5 to 50 volumes

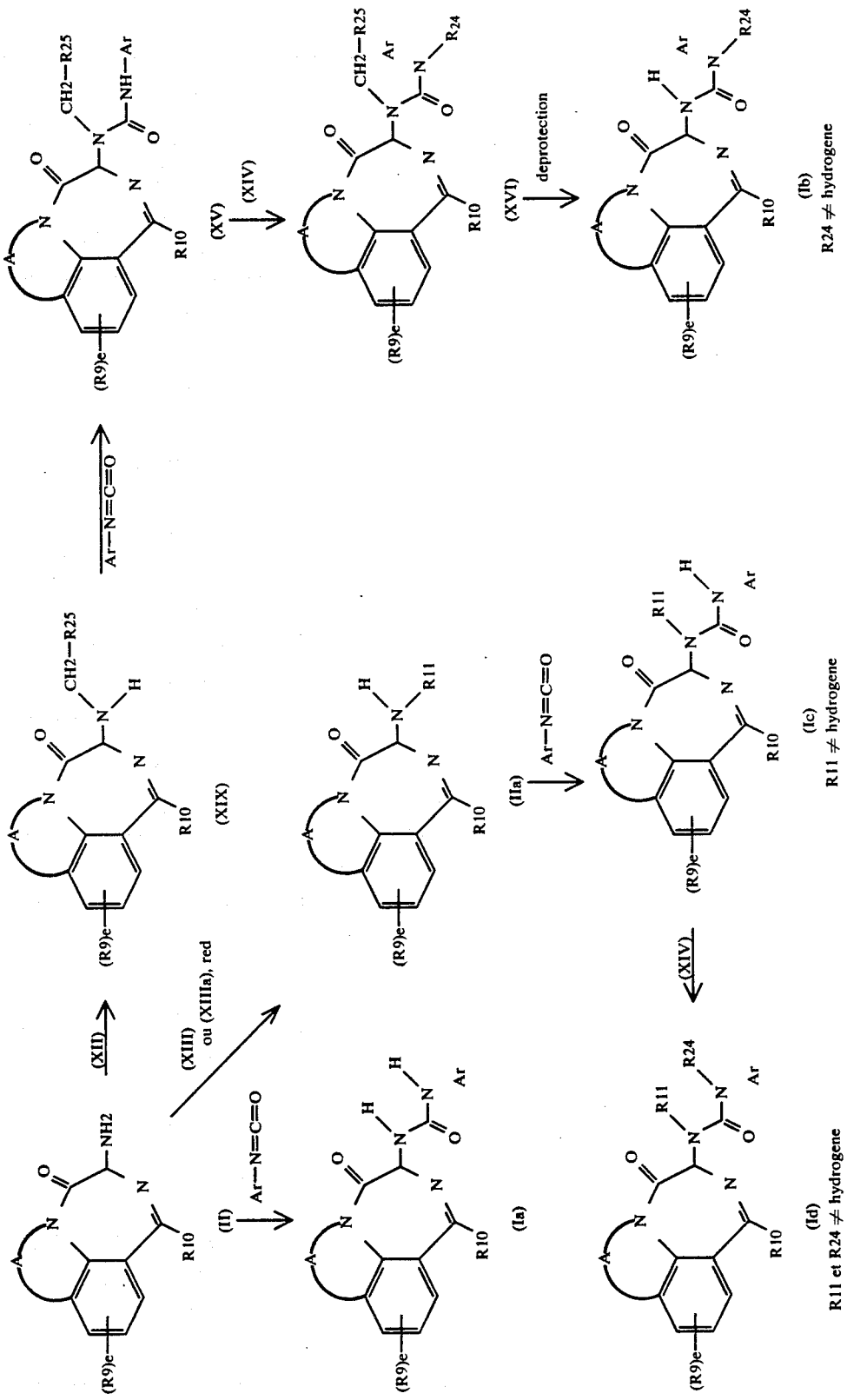

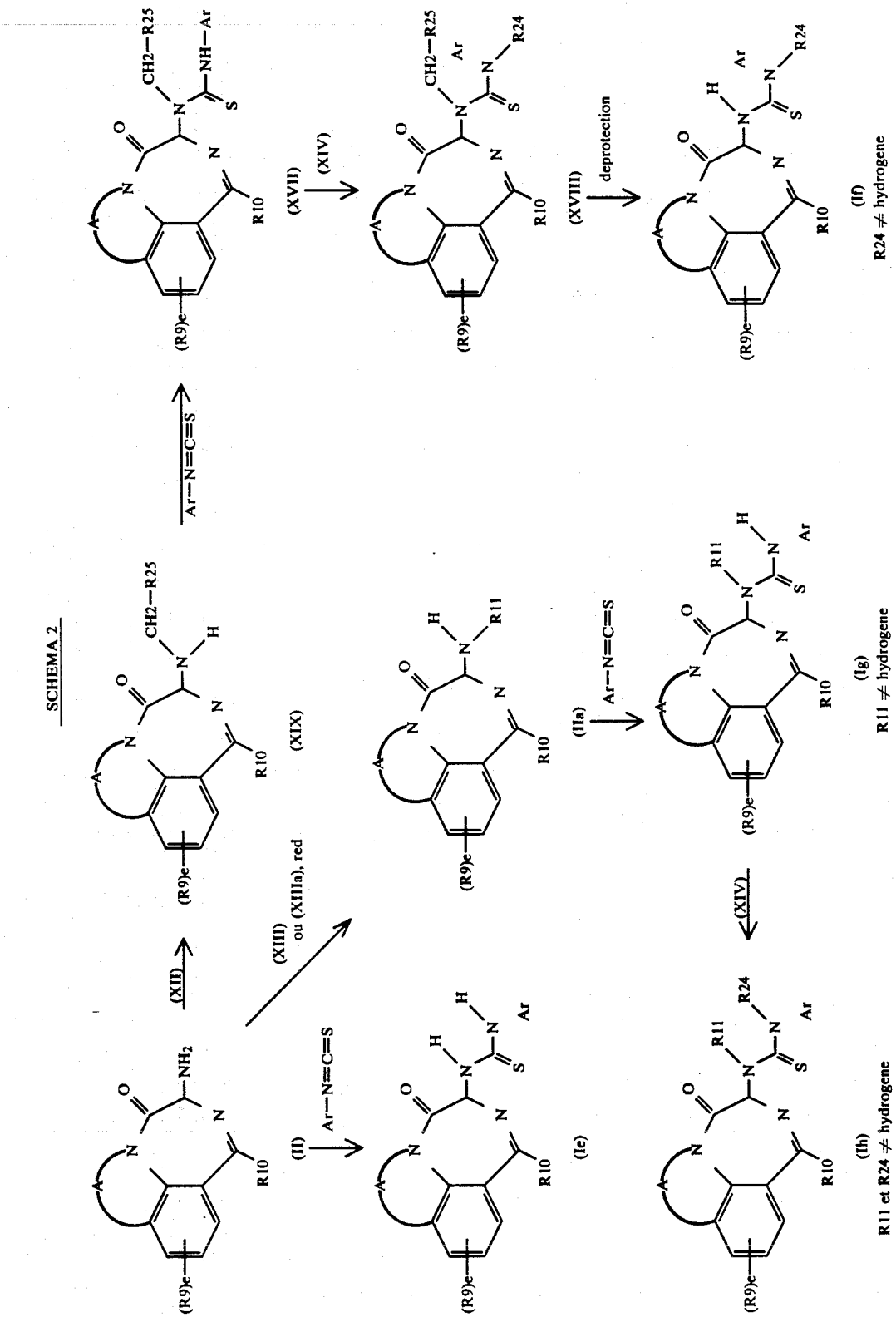

of an anhydrous organic solvent, for example a chlorinated hydrocarbon such as dichloromethane or chloroform, a linear or cyclic ether oxide such as dimethoxy-1-2-ethane, tetrahydrofuran or dioxane, an aprotic polar solvent such as pyridine, dimethylsulphoxide or dimethylformamide or any other suitable solvent to induce a condensation reaction or again a suitable mixture of two or more of these solvents, to which is added one equivalent of an agent capable of reacting with the amine function of the compound of formula (II) in order to yield a urea, such as a compound of formula Ar—N-H—CO—R51, in which R51 is halogen, p-nitrophenoxy or an imidazolyl group or preferably with a possibly substituted arylisocyanate Ar—N=C=O. In this case, stirring is carried out between −20° C. and the boiling point of the mixture for a period between ten minutes and several hours, a period between ten minutes and one hour being in general sufficient to ensure completion of the reaction. The reagent medium, possibly diluted with one of the solvents referred to above is then evaporated and the residual gross product purified.

(ii) Preparation of compounds (Ib) (Scheme 1)

In the case where R11 is hydrogen, R13 is N(R24), R24 being lower alkyl, and R12 is oxygen, the following procedure may be followed: A compound of formula (II) is dissolved in 5 to 50 volumes of water or of organic solvent, for example a chlorinated hydrocarbon such as dichloromethane or chloroform, a linear or cyclic ether oxide such as dimethoxy-1,2-ethane, tetrahydrofuran or dioxane, an aprotic polar solvent such as pyridine, dimethylsulphoxide of dimethylformamide or any other suitable solvent to induce a condensation reaction or again a suitable mixture of two or more of these solvents, to which is added one or more equivalents of a mineral base such as a hydroxide or an alkaline or alkaline earth carbonate or an organic base such as a tertiary aliphatic amine, preferably triethylamine, after which, at a temperature between 31 20° C. and the boiling point of the mixture, a quantity less than one equivalent of a compound of formula (XII) R25-CH2X, in which X represents a halogen or a pseudo-halogen, is added. The duration of this addition may be between a few minutes and a few hours, a duration of one to two hours being generally suitable. Stirring is carried out between −20° C. and the boiling point of the mixture for a period of between one and several hours, a period between two and four hours being in general sufficient to ensure completion of the reaction. The reagent medium, after possible filtration of the salts, is diluted with water and the product extracted with an organic solvent immiscible in water, for example a halogenated hydrocarbon, an ether oxide, an aliphatic or aromatic hydrocarbon or an ester. The organic phase after any necessary washing is concentrated under reduced pressure and the residual gross product purified to separate the reaction subproducts. This yields the benzylamine of formula (XIX).

Another method of preparing a benzylamine (XIX) based on an amine (II) consists in dissolving the compound (II) in 5 to 50 volumes of a protic organic solvent for example an alcohol, preferably methanol and adding to it at a temperature between 0° C. and the reflux temperature of the mixture a stoichiometric quantity of compound (XIIa) R25-CHO, previously defined above. The suspension is stirred and a sodium cyanoborohydride suspension or solution in 5 to 50 volumes of a solvent such as that described above is added. The addition is effected over a period between a few minutes and a few hours, a period of thirty minutes being in general suitable. At the end of this addition process the mixture is stirred for a period of time sufficient to ensure completion of the reaction, this period being determined by thin-layer chromatography, after which the mixture, having been brought to a temperature close to ambient temperature, is filtered, concentrated under reduced pressure and diluted with water, and the product is then extracted with an organic solvent, immiscible in water, and after evaporation of the solvent the residual gross product is purified.

This reducing amination may also be carried out as follows: a compound (II) is dissolved in 5 to 50 volumes of a protic organic solvent for example an alcohol, preferably methanol, to which are added a stoichiometric quantity of an organic base such as for example a tertiary amine, preferably triethylamine, then at a temperature between 0° C. and the reflux temperature of the mixture a stoichiometric quantity of compound (XIIa) R25—CHO. The suspension is returned to a temperature close to ambient temperature and transferred to an autoclave where it is treated at a temperature close to ambient temperature with hydrogen under a pressure between atmospheric pressure and 50 atmospheres for a period between thirty minutes and twenty four hours in the presence of a hydrogenation catalyst such as a noble metal finely divided and deposited on a support, a catalyst such as palladium (10%) on finely divided charcoal being suitable. The catalyst is then eliminated by filtration, the mixture concentrated under reduced pressure and diluted with water, and the product is then extracted with an organic solvent, immiscible in water, and after evaporation the residual gross product is purified.

The compound of formula (XIX) is then reacted with an arylisocyanate in similar fashion to compound (I) above in paragraph (i), thus yielding a urea of formula (XV) which is dissolved in 10 to 100 volumes of an anhydrous organic solvent, for example an aromatic hydrocarbon or a linear or cyclic ether such as tetrahydrofuran or in an aprotic polar solvent such as dimethylformamide, hexamethylphosphorotriamide, dimethylsulphoxide, N-methylpyrrolidinone or sulpholane (tetramethylenesulphone) or again in a mixture of these solvents. The solution is maintained at a temperature between −50° and 0° C. and 2 to 4 equivalents of a basic agent, capable of displacing the proton located on the nitrogen of the amide function such as for example a lower alcoholate of an alkaline metal preferably potassium tertiobutylate or tertioamylate, are added to it. The mixture is stirred for a period between 10 and 60 minutes and a stoichiometric or slightly higher quantity of a compound(XIV) R24-R39, in which R24 and R39 have the connotations defined above, is added to it, followed by stirring for a period between 10 and 60 minutes. The reagent medium is then concentrated, the salts present in the medium filtered, the medium possibly diluted with water and the product extracted with an organic solvent, immiscible in water, and after evaporation of the solvent the urea of formula (XVI) is purified.

The urea is then dissolved in 10 to 100 volumes of liquid ammonia, possibly with the addition of a quantity between 0 and 50% of a cosolvent such as ether oxide, preferably tetrahydrofuran or dioxane, in order to improve the solubility of the urea, and small portions of a quantity between 1 and 3 sodium equivalents added to it. A blue colouring is formed after the addition of each portion, which disappears rapidly (in 15 to 30 seconds). The addition process is halted when the blue colouring persists for more than one minute. Excess ammonium chloride is added, after which it is diluted with a water-insoluble organic solvent for example methylene chloride or ethylacetate and water. The product is then extracted in the organic solvent and after evaporation the benzodiazepine of formula (Ib) is purified.

(ii) Preparation of compounds (Id) (Scheme 1)

In the case where R11 is lower alkyl, R13 is N—R24, R24 being lower alkyl, and R12 is oxygen, alkylation is carried out of a benzodiazepine (Ic), the preparation of which is described in paragraph (i) above, in the same fashion as for the preparation of a benzodiazepine (Ib) in order to obtain the intermediate product (XVI) by alkylation of compound (XV) as described in paragraph (ii) above.

(iv) Preparation of compounds (Ie) and (Ig) (Scheme 2)

In the case where R13 is N(R24) and R12 is a sulphur atom, the following procedure may be adopted in particular:

A compound of formula (II) or (IIa) is dissolved in 5 to 50 volumes of an anhydrous organic solvent, for example a chlorinated hydrocarbon such as dichloromethane or chloroform, a linear or cyclic ether oxide such as dimethoxy-1,2-ethane, tetrahydrofuran or dioxane, an aprotic polar solvent such a pyridine, dimethylsulphoxide or dimethylformamide or any other solvent capable of inducing a condensation reaction or again a suitable mixture of two or more of these solvents, to which is added one equivalent of an agent capable of reacting with the amine function of compound (II) to yield a thiourea, such as for example a possibly substituted arylisothiocyanate. Stirring is carried out between $-20°$ C. and the boiling point of the mixture for a period between ten minutes and sixteen hours, a period between ten minutes and one hour being in general sufficient to ensure completion of the reaction. The reagent mixture, possibly diluted with one of the solvents cited above, is then evaporated and the product purified.

(v) Preparation of compounds (If) (Scheme 2)

In the case where R11 is hydrogen, R13 is N(R24), R24 being lower alkyl and R12 sulphur, the same procedure is followed as for the preparation of a benzodiazepine (Ib) but replacing the arylisocyanate by an arylisothiocyanate, in order to obtain in succession a benzylamine (XIX), a thiourea (XVII), a tetrasubstituted thiourea (XVIII) and then, after elimination of the protective group R25—CH2—, a benzodiazepine of formula (If). It is however to be noted in this case that the first method of eliminating the protective group is unsuitable since the sulfur would poison the metal catalyst.

(vi) Preparation of compounds (Ih) (Scheme 2)

In the case where R11 is lower alkyl, R13 is N—R24, R24 being lower alkyl, and R12 is sulphur, the procedure is based on a benzodiazepine of formula (Ig), as described in paragraph (iii) above for the preparation of a benzodiazepine (Id) based on a benzodiazepine (Ic).

PREPARATION OF A RACEMIC COMPOUND OF FORMULA (II) OR (IIa)

The preparation of racemic compounds of formula (II) and (IIa) based on benzodiazepines-[1,4] of formula (III) is illustrated in scheme 3 and described in detail below:

(i) Where R11 is hydrogen (formula (II))

The amine (II) may be prepared by amination in the $\alpha$-position in relation to the carbonyl of a benzodiazepine-[1,4]-one (III) (scheme 3), in which A, R9, R10 and e have the connotation defined above, with a hydroxylamine derivative or chloramine.

Amination of the benzodiazepine-[1,4]-one (III) may also be carried out in two stages, the first stage consisting in inducing a reaction on an oximation reagent of formula (XI):

in which h is 1 or 2 and R35 is lower alkoxy or chlorine when h is 1 and is NO2 and h is 2, in order to obtain the oxime of formula (IV), which is shown in scheme 3 and in which A, R9, R10 and e have the connotation defined above, which is then isolated, and the second stage consists in the catalytic reduction of the oxime by hydrogen in the presence of a reducing catalyst or by reaction with zinc in the presence of acetic acid or with stannour chloride in the presence of hydrochloric acid, in order to obtain the aminated derivative (II).

The amine (II) may again be prepared by reacting a benzodiazepine 1,4-one (III) in a basic medium on an appropriate reagent in order to introduce a nitride function on a carbanion in order to obtain a nitride of formula (V) (Scheme 3), in which A, R9, R10 and e have the connotation defined above; which is isolated and then reduced with a reducing agent.

To prepared a compound (II) in a single based on a compound (III), the compound (III) is dissolved in 10 to 100 volumes of an anhydrous organic solvent, such as for example an aromatic hydrocarbon or a linear or cyclic ether, such as for example tetrahydrofuran, or in an aprotic polar solvent such as dimethylformamide, hexamethylphosphorotriamide,

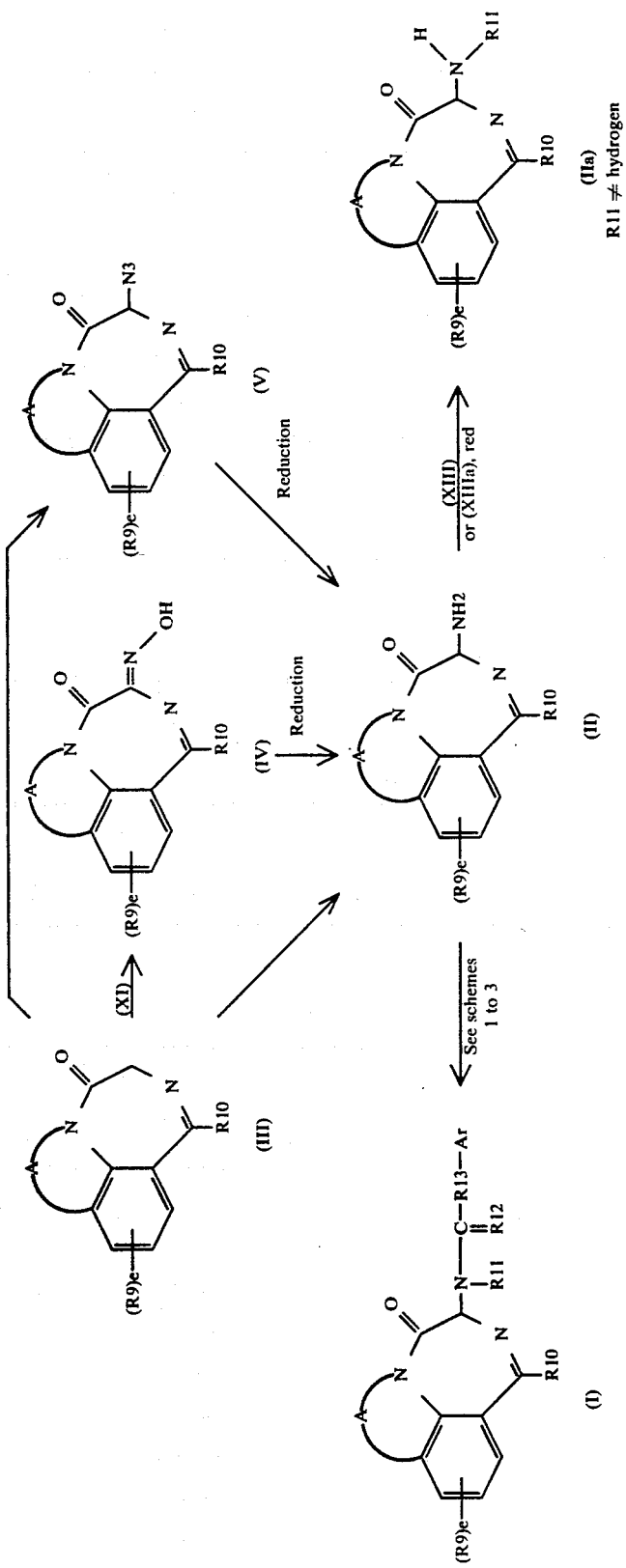

dimethylsulphoxide, N-methylpyrrolidinone or sulpholane (tetramethylene-sulphone) or again in a mixture of these solvents. The solution is maintained at a temperature between −50° and 0° C., during which 2 to 4 equivalents are added of a basic agent capable of displacing the proton in the α-position of the carbonyl group of the diazepine ring such as for example a lower alcoholate of an alkaline metal, preferably potassium tertiobutylate or tertioamylate. The mixture is stirred for a period between 10 and 60 minutes, during which 3 to 20 equivalents are added of an amination reagent such as for example a hydroxylamine derivative, O-(2,4-dinitrophenyl)-hydroxylamine or O-(diphenyl-phosphinyl)-hydroxylamine or O-(2,4,6-trimethylphenyl-sulphonyl)-hydroxylamine or chloramine then stirred for a period between 10 and 60 minutes. The reagent medium is then concentrated, the salts present in the medium filtered, the medium possibly diluted with water and the product extracted with an organic solvent, immiscible in water, and after evaporation of the solvent the product is purified by the usual methods.

To prepare a compound (II) in two stages based on a compound (III) by isolating an intermediate compound of formula (IV) comprising an oxime function, the following procedure is followed (preferred method of operation):

A compound (III) is dissolved in 10 to 100 volumes of an anhydrous organic solvent such as for example an aromatic hydrocarbon or a linear or cyclic ether, such as for example tetrahydrofuran, or in an aprotic polar solvent such as dimethylformamide, hexamethylphosphorotriamide, dimethylsulphoxide, N-methylpyrrolidone or sulpholane or again in a mixture of these solvents. The temperature is maintained between −50° and 0° C., during which 2 to 4 equivalents are added of a basic agent capable of displacing the proton in the α-position of the C=O, such as for example a lower alcoholate of an alkaline metal preferably potassium tertiobutylate or tertioamylate. The mixture is stirred for a period between 10 and 60 minutes and 3 to 20 equivalents of a lower alkyl nitrite added, preferably isoamyl nitrite or nitrosyl chloride (NOCl) or again nitrogen tetroxide (N2O4) and the mixture allowed to return to ambient temperature, after which stirring is carried out for a period between 10 and 60 minutes. The reagent medium is then neutralized by the addition of a 1:10 acetic acid solution and the product extracted in one or more operations with an organic solvent, imiscible in water, such as for example an aliphatic or aromatic hydrocarbon, a halogenated hydrocarbon, an ether or a lower alcohol ester of a lower carboxylic acid. The product is purified after evaporation of the solvent. The intermediate compound of formula (IV) is then transformed into an aminated compound (II) by suspension in 5 to 100 volumes of an organic solvent such as for example a lower aliphatic alcohol or a lower aliphatic alcohol ester of a lower carboxylic acid in the presence of a hydrogenation catalyst such as for example Raney's nickel, rhodium on charcoal or ruthenium on charcoal which is the generally preferred catalyst. The suspension is stirred in a hydrogen atmosphere under a pressure between atmospheric pressure and thirty atmospheres for a period between one and fifty hours at a temperature between 0° C. and 80° C.; a pressure slightly above atmospheric pressure, a temperature of the order of 70° C. and a stirring period of two hours being in general sufficient to ensure completion of the reaction. The reagent medium is then filtered and the catalyst washed several times with a solvent of the same type as that cited above. The produce is purified after evaporation of the solvent.

This reduction may also be carried out not by catalytic but by chemical means (in stoichiometric fashion) by bringing the compound (IV) into contact with a reducing agent such as for example zinc in acetic acid or stannous chloride in hydrochloric acid or again nickel boride (a reagent prepared by the action of sodium borohydride on divalent nickel chloride).

To prepare a compound (II) in two stages based on a compound (III) by isolating an intermediate compound (V) comprising an azide function, the following procedure is adopted:

A compound (III) is dissolved in 5 to 100 volumes of an anhydrous organic solvent, for example an aromatic hydrocarbon or a linear or cyclic ether such as tetrahydrofuran, or in a polyether (solvent of the so-called glymes series) or in an aprotic polar solvent such as dimethylformamide, hexamethylphosphorotriamide, dimethylsulphoxide, N-methylpyrrolidinone or sulpholane or again in a mixture of these solvents. The solution is maintained at a temperature between −50° C. and ambient temperature and 1 to 4 equivalents are added of a basic agent capable of displacing the proton in the α-position of the carbonyl of a compound (III), such as for example a lower alcoholate of an alkaline metal, preferably potassium tertiobutylate or tertioamylate, or lithium butylate or sodium hydride or sodium amidide. The mixture is stirred for a period of between 10 minutes and 6 hours and 1 to 5 equivalents added of a reagent capable of introducing an azide function on a carbanion, the preferred reagent being tosyl azidide, and the mixture possibility allowed to return to room temperature, after which stirring is carried out for a period between 10 minutes and 5 hours at a temperature between ambient temperature and the reflux temperature of the mixture. The salts present in the reagent medium are then possibly filtered, the reagent medium neutralized by the addition of a 1:10 acetic acid solution and the product extracted in one or more operations with an organic solvent, immiscible in water, such as for example an aliphatic or aromatic hydrocarbon, a halogenated hydrocarbon, an ether or a lower alcohol ester of a lower carboxylic acid, the organic phase is then possibly washed with a dilute acid or mineral base solution and then with water. The product is purified after evaporation of the solvent. The intermediate compound (V) is then transformed into an aminated compound (II) in the following manner:

A compound (V) is suspended in 5 to 100 volumes of an organic solvent such as for example a lower aliphatic alcohol, a lower aliphatic alcohol ester of a lower carboxylic acid, an aromatic solvent such as for example benzene, toluene or pyridine, water or again a mixture of these solvents and 1 to 10 equivalents added of a reducing agent such as for example vanadium chloride II (VCl2) in aqueous solution, sodium borohydride (in the presence of methanol), hydrogen sulphide or Raney's nickel. The reagent mixture is stirred at a temperature between ambient temperature and the reflux temperature of the mixture for a sufficiently long period to ensure completion of the reaction (depending on the nature of the reducing agent used, this period which is determined by thin-layer chromatography may vary from 10 minutes to several hours) then possibly cooled, filtered to eliminate any precipitate that may be present, neutralized, diluted and the solvent eliminated by distillation under vacuum, after which the product is purified.

It is also possible to carry out this reduction not by stoichiometric but by catalytic means, bringing the compound (V) into contact with a reducing agent in the presence of a reduction catalyst such as for example ammonium formate in the presence of palladium on charcoal or hydrogen (under a pressure between 1 to 5 atmospheres) in the presence of palladium deposited on calcium carbonate (so-called Lindlar catalyst). After filtration of the catalyst, the aminated product of formula (II) is isolated in a manner similar to that described above.

(ii) Where R11 is lower alkyl (formula (IIa))

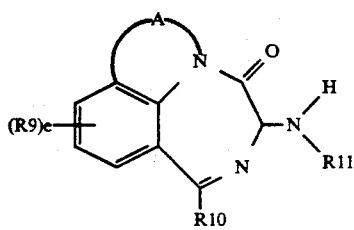

(IIa)

R11 different from hydrogen

To prepare a compound of formula (IIa) based on a compound (II), the procedure described above for the preparation of benzodiazepine of formula (Ic) (scheme 1) is followed, but using according to the particular case:
- a reagent of formula (XIII) for direct alkylation of the amine,
- or a reagent of formula (XIIIa) instead of reagent (XII) or (XIIa) in the case of a reducing amination.

PREPARATION OF COMPOUNDS OF FORMULA III

Compounds (III) have been prepared by the method described in the literature which is briefly described below.

It consists in principle in treating an indoline or a substituted tetrahydroquinoline in suitable fashion with one equivalent of borotrichloride, then with a suitably substituted benzonitrile, then with aluminium chloride and heating the mixture, possibly dissolved in an organic solvent, to a temperature between 80° and 150° C.

After hydrolysis, this yields an aminoketone. The method is described in detail in: Adachi, M. et al., Chem. Pharm. Bull., 1985 33 1826 and in Kuzuyuki, S. et al, Chem. Pharm. Bull., 1985 33 1836.

This is followed by the cyclic conversion of the aminoketone into benzodiazepine (II) by the method described by Hester, J. B. et al. (J. Med. Chem., 1970 13 827). It consists in treating an aminoketone with bromacetyl chloride or iodoacetyl chloride in an organic solvent in the presence of one equivalent of an organic base, in order to obtain a haloacetamide which is reacted with an ammonia solution in an organic solvent in order to obtain a benzodiazepine of formula (III).

PREPARATION OF AN OPTICALLY ACTIVE COMPOUND OF FORMULA (II) OR (IIa)

The preparation of compounds (II) i pure enantiomer forms is shown in scheme 4 and set out in detail below.

A racemic benzodiazepine (II) or (IIa) is condensed with a molecule deriving from an optically active amino acid, natural or not, belonging to the D or L series, of formula (VII):

(VII)

SCHEME 4
SEPARATION OF (II) ISOMERS

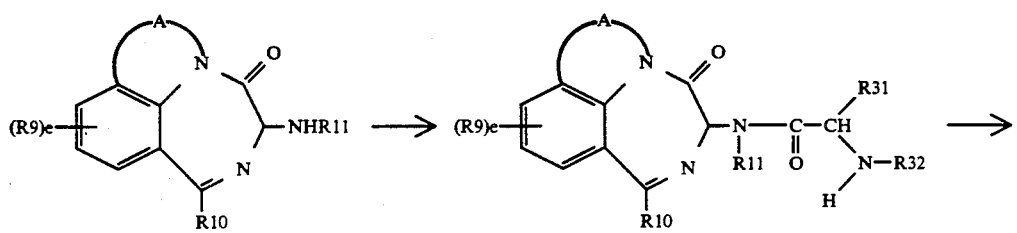

(II): R11 = hydrogene
(IIa): R11 ≠ hydrogene
racenique (VIII) racenique

-continued
SCHEME 4
SEPARATION OF (II) ISOMERS

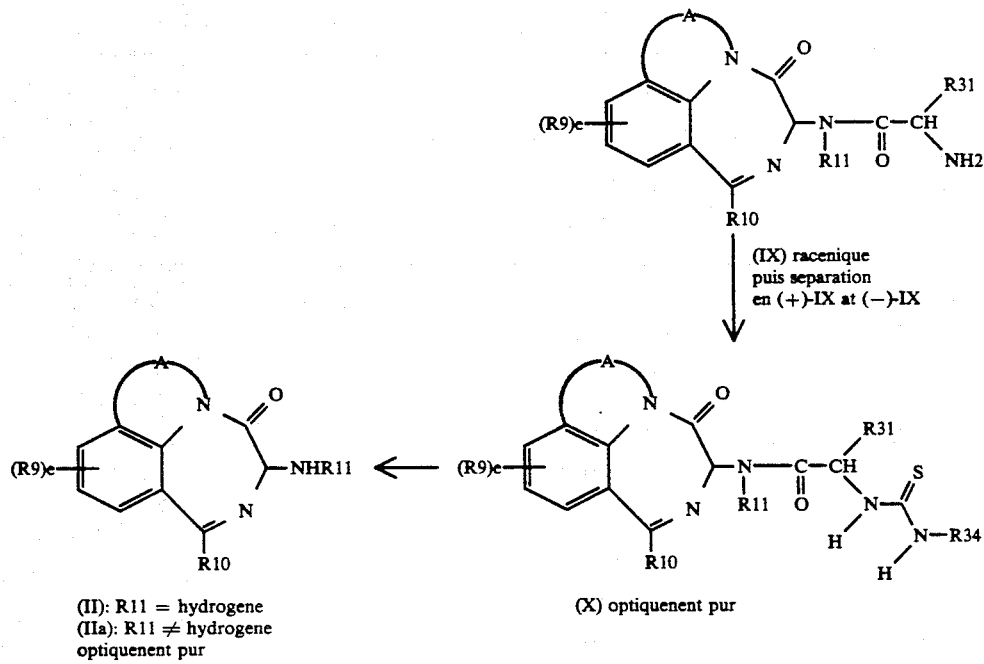

(II): R11 = hydrogene
(IIa): R11 ≠ hydrogene
optiquenent pur (X) optiquenent pur R31 being
- an alkyl group having from 1 to 6 carbon atoms possibly substituted by a hydroxyl group, a thioalkyl group having from 1 to 6 carbon atoms in the alkyl group or a carboxyl or carbonylamino group,
- an aryl group comprising one or two rings, possibly substituted with a hydroxyl group, and which is in particular phenyl or benzyl,
- an aralkyl group having one or two aromatic rings, the alkylic portion of which comprises 1 to 6 carbon atoms, possibly substituted on the ring by one or more halogen, hydroxy or methoxy groups,
- a heterocyclic structure having five or six chain links and one or two heteroatoms selected from among nitrogen, oxygen and sulphur,
- an indolyl-3-methyl group,
- an imidazolyl-4-methyl group.

R31 will be preferably the isobutyl group and the amino acid will belong to the L series.

R32 being a group which can be easily eliminated in order to regenerate the free amine and may be
- an oxycarbonyl radical of R38—O—CO-structure in which R38 is an alkyl group comprising one to six carbon atoms, or an aryl group, possibly substituted by one or more methoxy, halogen or nitro groups, for example benzyl, p-chlorobenzyl, p-bromobenzyl, p-nitrobenzyl, fluoronyl-9-methyl p-methoxybenzyl, dichloro-2,4-benzyl, dichloro-2,6-benzyl, t-amyl, isopropyl, adamantyl,
- an alkanoyl or alkenoyl group comprising 1 to 6 carbon atoms or an acyl group such as formyl, trifluoroacetyl, phthalyl,
- p-toluenesulphonyl,
- p-nitrosulphenyl, R38 being preferably the tertiobutyl group.

R33 being a hydroxy group, an azide group (—N3), an imidazole-1-yl group, a —O—CO—O—R36 group, R36 being possibly an obstructed alkyl radical comprising three to six carbon atoms or a —OR37 group, R37 being an aromatic group comprising one or two rings possibly substituted by one or more nitro or halogen radicals. R37 is preferably benzotriazolyl-1.

The condensation is carried out under suitable conditions to transform a compound of formula (II) into a compound of formula (I). This yields a compound having the general formula (VIII) in which A, R9, R10, R31, R32 and e have the connotations given above, in the racemic form. The protective group on the nitrogen (R32) is then removed, so that the free amine of formula (VI) is obtained in the racemic form. This removal of the protection may be effected by hydrolysis:
- either in a acid medium, in the presence of a strong mineral or organic acid such as hydrochloric acid, sulphuric acid, hydrofluoric acid, hydrobromic acid or a sulphonic acid, for example para-toluenesulphinic acid or methanesulphonic acid, or again acetic acid possibly substituted by one to three chlorine or fluorine atoms, formic acid or any other suitable acid in a solvent or a mixture of aqueous or organic solvents, such as a carboxylic acid, a halogenated aliphatic hydrocarbon, an aromatic hydrocarbon possibly substituted by a halogen or hydroxy group, an aliphatic alcohol possibly substituted by one or more halogen atoms, such as for example ethanol or trifluoroethanol or again a linear or cyclic aliphatic ether such as for example dimethyoxy-1,2-ethane, dioxane or tetrahydrofuran. The preferred acid hydrolysis method consists in dissolving the compound in a solution of about 10% trifluoroacetic acid in methylene chloride and stirring for a period of between a few minutes and few hours at a temperature within the range from 0° C. to the reflux temperature of the reagent mixture.
- Or in a basic medium in certain cases as for example where the protective group R32 is C(=O-

)—O—R38 and R38 is the fluorenyl-9-methyl group, the solvent used being an aqueous or organic solvent or solvent mixture such as a halogenated aliphatic hydrocarbon, a protic or aprotic dipolar solvent such as for example dimethylformamide, dimethylsulphoxide, tetramethylenesulphone (sulpholane), N-methylpyrrolidone, acetonitrile or N,N-dimethylacetamide; an aliphatic alcohol, an aliphatic alcohol ester of carboxylic acid, a linear or cyclic ether; the basic agent being possibly a mineral base such as an alkaline metal hydroxide or an organic base such as an aliphatic tertiary amine, for example triethylamine, diisopropylethylamine, N-methylpyrrolidine or again N-methylmorpholine.

Or again by catalytic hydrogenation, the catalyst used being possibly a noble metal for example palladium or again an oxide of one of these metals deposited on a support, the nature of the suitable catalyst varying according to the nature of the R32 group; when R32 is R38—O—CO— and R38 is benzyl, the catalyst may be palladium on charcoal.

The amino acid derivative thus obtained (IX) is separated into its diastereoisomers by chromatography, yielding the two isomers of the amine (IX).

This is followed by Edman degradation on each of the diastereoisomer compounds (IX), in order to obtain the two enantiomers (R) and (S) of the amine (II).

The Edman degradation technique consists of:

reacting an arylisothiocyanate of formula R34—N=C=S on the free amine function of an optically active compound of formula (IX) in order to obtain a thiourea of formula (X); the R34 group being an aryl radical such as phenyl or naphthyl possibly substituted by one or more substituents chosen from among the halogens, the methoxy group or a lower alkyl group having 1 to 6 carbon atoms, the phenyl group being most generally used. The reaction is carried out in a solvent which is inert in relation to the isothiocyanate function, such as a halogenated aliphatic hydrocarbon, an aromatic hydrocarbon possibly substituted by a halogen group, an aliphatic ester of an aliphatic alcohol, an aprotic dipolar solvent for example dimethylformamide, dimethylsulphoxide, tetramethylene sulphone (sulpholane), N-methylpyrrolidone, acetonitrile or N,N-dimethylacetamide or again a linear or cyclic aliphatic ether for example dioxane or tetrahydrofuran. Preference is normally given to the induction of this reaction in methylenechloride at a temperature between 0° C. and the reflux temperature of the reagent mixture, the reaction being completed at the end of a period of between a few minutes and a eight hours.

forming a ring and cutting the thiourea thus obtained (X) to obtain the optically active amine (II). This can be done in one or two stages. Normal preference is for the two stage procedure without isolating the intermediate cyclic compound, thus avoiding the need for purification. The technique generally used is to dissolve the thiourea in five to one hundred volumes of a solution having a concentration between 5% and 100% of a strong acid such as for example trifluoroacetic acid in an organic solvent for example a halogenated hydrocarbon, preferably methylene chloride and stirring this solution at a temperature between 0° C. and the reflux temperature of the reagent mixture for a period of between a few minutes and sixteen hours.

The isomers of the amine (II) may also be separated by salt formation and crystallization, followed by filtration of the salt thus obtained. The process consists in dissolving the racemic amine (II) in a solution of an optically active acid, known for the purpose of separating organic bases, such as for example mandelic acid, dibenzoyltartaric acid, di-p-tolyoyltartaric acid, camphosulphonic acid, p-nitrogenzoylglutamic acid, tartaric acid and binaphthyl phosphoric acid, in an aqueous or organic solvent such as for example a lower aliphatic alcohol, acetone, acetonitrile or any other solvent capable of inducing the selective crystallization of one of the diastereoisomer salts. L(+)-tartaric acid or (+)-dinaphthylphosphoric acid are the preferred compounds, dissolved in acetone or acetonitrile.

The invention covers also a pharmaceutical for the treatment of Zollinger-Ellison syndrome, gastro-intestinal disorders and those of the pancreas and gall bladder, disorders of the central nervous system and pain, characterized in that is comprises a benzodiazepine according to the invention.

EXAMPLES

The invention is illustrated by means of the following examples.

Unless otherwise specified, the methods used during syntheses and analyses are summarized below.

The melting points were recorded on the capillary tube of a Mettler apparatus and have not been corrected. The nuclear magnetic resonance spectra were recorded on a JEOL FX-90Q (90 MHz) spectrometer, tetramethylsilane being used as the internal standard. The spectra have been described in the following way: chemical displacement (expressed as ppm in relation to the internal standard), multiplicity, integration intensity and possibly the coupling and attribution constant. The infrared spectra have been recorded in the form of a potassium bromide pellet on a Shimadzu IR-435 photometer. Flash chromatographs have been recorded as described by Still on silicagel (E. MERCK article 4063) (Still, W. C., M. Kahn and A. Mitra. J. Org. Chem., 1978 43 2923). The thin-layer chromatographs were carried out on 60F-254 silica plate, 0.25 mm in thickness (E. Merck article 5714). The plates were examined under UV light or developed with iodine, Dragtendorff reagent or toluidine reagent. The high pressure liquid chromatographs (HPLC) were carried out on a Jobin-Yvon instrument. The rotational capacity was measured on a Polartronic instrument in a 10 cm long cuvette at normal temperature.

PREPARATION OF THE COMPOUNDS OF THE INVENTION

Example 1:
(4R,S)-N-(keto-3-phenyl-6-tetrahydro-1,2,3,4-pyrrolo[3,2,1-j,k] benzodiazepine[1,4]-yl-4)-N'-(methyl-3-phenyl-)-urea Formula (I) A=—(CH2)2—; R9=H; R10=phenyl; R11=H; R12=O, R13=NH; Ar=methyl-3-phenyl Stage 1a: Transformation of a compound of formula (III) into a compound of formula (IV).

A solution of 26.3 g phenyl-6-tetrahydro-1,2,3,4-pyrrolo[3,2,1-j,k] benzodiazepin-[1,4]-one-3 (100 moles) is introduced into a mixture of 500 ml anhydrous toluene and 250 ml anhydrous tetrahydrofuran in a tricol flask under nitrogen atmosphere. The solution is cooled to −20° C. and 37.1 g anhydrous potassium butylate (330 mmoles) added to it, as a result of which the solution turns a brownish red. After 30 minutes stirring at −20° C., 20.1 ml isoamyl nitrite (150 mmoles) are added, the mixture allowed to return to ambient temperature with continued stirring for 30 minutes. 50 ml acetic acid is then added, followed by 500 ml water. The organic phase is decanted and the aqueous phase re-extracted with methylene chloride (3 times 200 ml). The organic extracts are evaporated under reduced pressure and the residue purified by flash chromatography on silica, the elution agent used being a mixture of increasing polarity of acetone in methylene chloride.

This yields 23.3 g hydroxyimino-4-phenyl-6-tetrahydro-1,2,3,4-pyrrolo [3,2,1-j,k]benzodiazepin-[1,4]-one-3 in the form of a yellow solid (80%). MP=215° C. (decomposition).

| NMR: | | | | |
|---|---|---|---|---|
| 11.20 ppm | s | 1 proton | | OH |
| 7.80–7.00 ppm | m | 8 protons | | aromatic |
| 4.35 ppm | t | 2 protons | J = 8 Hz | CH2—N |
| 3.20 ppm | t | 2 protons | J = 8 Hz | CH2 |

Benzylic IR: 3300, 3050, 2800, 1665, 1620, 1600, 1570, 1525, 1515, 1340, 1215, 1150, 1000 cm$^{-1}$.

Stage 1b: Transformation of a compound of formula (IV) into a compound of formula (II): preparation of amino-4-phenyl-6-tetrahydro-1,2,3,4-pyrrolo [3,2,1-j,k]benzodiazepin-[1,4]-one-3. Formula (II): A=—(CH2)2—; R9=H; R10p32 phenyl (Ia).

FIRST METHOD

A suspension of 100 g Raney's nickel and 23.3 g hydroxyimino-4-phenyl-6-tetrahydro-1,2,3,4-pyrrolo[3,2,1-j,k]benzodiazepin [1,4]one -3 in 1 l methanol is introduced into a hydrogenation reactor. The suspension is stirred at ambient temperature until hydrogen absorption is complete (after about 20 hours). The suspension is filtered and washed with five times 200 ml methanol. The methanol is evaporated under reduced pressure, leaving a viscous oily residue which is purified by flash chromatography in a silica column, the elution agent used being a mixture of increasing polarity of methanol in methylene chloride. This yields 11.0 g amino-4-phenyl-6-tetrahydro-1,2,3,4-pyrrolo[3,2,1-j,k]-benzodiazepin-(1,4-]one-3 (58%) in the form of oil which is utilized immediately in the following reaction. TLC: CH2Cl2/MeOH 95/5 Rf=0.20.

| NMR: | | | |
|---|---|---|---|
| 7.65–7.00 ppm | m | 8 protons | aromatics |
| 4.80–4.20 ppm | m | 2 protons | CH2—N |
| 4.20–3.60 ppm | m | 3 protons | CH—NM2 |
| 3.40–2.80 ppm | m | 2 protons | CH2Ar |

IR: 3350, 1675, 1600, 1560, 1440, 1340, 1240, 1100, 730, 690 cm$^-$.

SECOND METHOD 9.6 g ruthenium on 5% charcoal is introduced under nitrogen into a reactor capable of withstanding a pressure of 12 bar. Hydrogenation of the ruthenium is continued for 2 hours at 20° C. under 10 bar hydrogen pressure. 32 g (110 mmoles) hydroximino-4-phenyl-6-tetrahydro-1,2,3,4-pyrrolo[3,2,1-j,k] benzodiazepin-[1,4]-one-3 are added under nitrogen atmosphere. The reactor is returned to a hydrogen pressure of 8 bar and heated gradually to 72° over a 2 hour period. This is followed by cooling, filtration on silica and rinsing with methanol. The yield after chromatography on silica in methanol-enriched methylene chloride is 29.0 g (94%).

Stage 1c: Transformation of a compound of formula (II) into a compound of formula (I). Case where R13=NH.

5.54 g (20 mmoles) (4R,S)-amino-4-phenyl-6-tetrahydro-1,2,3,4-pyrrolo [3,2,1-j,k]benzodiazepin-[1,4]-one-3, obtained during the previous stage, and 100 ml methylene chloride are introduced into a dry flask, screened from the humidity by a nitrogen atmosphere and a calcium chloride protection. The mixture is cooled in a glacial bath, after which 2.66 g methyl-3-phenyl isocyanate (20 mmoles) are added. After 1 hour at ambient temperature, the solvent is evaporated and the residue chromatographed on a silica column in a methylene chloride mixture containing 10 vol. % acetone. This yields 6.06 g (74%) white solid.

MP: 180° C.

TLC: CH2C12/acetone 95/5 Rf=0.25.

| NMR: | | | |
|---|---|---|---|
| 8.95 ppm | s | 1 proton | Co—NH—AR |
| 7.70–6.70 ppm | s | 13 protons | ArH,NH |
| 5.17 ppm | d | 1 proton | CO—CH—N |
| 4.50 ppm | m | 1 proton | CH2N |
| 3.95 ppm | m | 1 proton | CH2N |
| 3.30 ppm | m | 2 protons | CH2Ar |
| 2.17 ppm | s | 3 protons | CH3Ar |

IR:3350, 1670, 1640, 1610, 1550, 1440, 1380, 1290, 1210 cm$^1$.

Example 2:
(4R)-N-(keto-3-phenyl-6-tetrahydro-1,2,3,4-pyrrolo[3,2,1-j,k]
benzodiazepine-[1,4]-yl-4)-N′-(methyl-3-phenyl-)-urea Formula (I): A=—(CH2)2—; R9=H; R10=phenyl; R11=H; R1232 O; R13=NH; Ar=methyl-3-phenyl; dextrorotatory isomer Stage 2a Preparation of phenyl-6-(N-(N-tertiobutyloxy-carbonyl-L-leucyl-)-amino]-4-tetrahydro-1,2,3,4-pyrrolo [3,2,1-j,k]benzodiazepine-[1,4]-one-3.

Formula (VIII): A=—(CH2)2—; R9=H; R10=phenyl; R11=H; R12=O; R13=NH; R31=isobutyl=R32=tertiobutyloxycarbonyl.

19.0 g (68.5 mmoles) of the amine, prepared in Example 1, Stage (b) are dissolved in methylene chloride (500 ml) in a tricol flask containing a calcium chloride protection and fitted with an immersion thermometer and a nitrogen inlet.

17.1 g Boc—L—leucine (68.5 mmoles) and 10.5 g hydroxy-1-benzotriazole hydrate (68.5 mmoles) are added, followed by the dropwise addition of 500 ml methylene chloride solution containing 14.1 g N,N′dicyclohexylcarbodiimide (68.5 mmoles). The mixture is stirred for 2 hours at 5° C. and allowed to return to ambient temperature. After 20 h, filtration is carried out of the insolubles and rinsing with abundant methylene chloride. The residue is evaporated and chromatographed on a silica column, eluting with acetone-enriched methylene chloride. The yield is 32.5 g (97%) purified product.

TLC: CH2Cl2/acetone 5% Rf=0.8.

| NMR: | | | | |
|---|---|---|---|---|
| 7.75 ppm | d | 1 proton | J = 8 Hz | CH—NM—CO |
| 7.60–6.90 ppm | m | 8 protons | | aromatics |
| 5.42 ppm | d | 1 proton | J = 8 Hz | CH—NH—Co |
| 5.10 ppm | d | 1 proton | | NC—CH—CO |
| 4.60 ppm | m | 1 proton | | CH2N |
| 3.95 ppm | m | 1 proton | | CH2N |
| 3.70–3.25 ppm | m | 3 protons | | CH2Ar, NH—CH—CO |
| 1.90–1.20 ppm | m | 3 protons | | CHCH2 |
| 1.45 ppm | s | 9 protons | | C(CH3)3 |
| 1.0 ppm | d | 6 protons | | (CH3)2 |

IR: 3300, 2900, 1710–1650, 1500, 1440, 1160, 1020 cm$^{-1}$.

Stage 2b: Preparation of (4R,S)-N-(-L-leucyl-)amino-4-phenyl-6-tetrahydro-1,2,3,4-pyrrolo[3,2,1-j,k]benzodiazepin-[1,4]-one-3.

Formula (IX): A=—(CH2)2—; R9=H; R10=phenyl; R11=H; R13=NH; R31=isobutyl 32.5 g (66 mmoles) of product from the preceding stage are dissolved in 300 ml methylene chloride. It is cooled in ice and 300 ml trifluoroacetic acid added to it in 1 minutes but without allowing the temperature to rise above 5° C. After 30 minutes stirring, evaporate to dryness. It is then redissolved in ethylacetate and normal soda, then washed with water, saturated with sodium chloride, dried and evaporated. This is followed by chromatography on silica, eluting with a mixture of increasing polarity of methanol in methylene chloride.

The yield is 24.0 g (72%) product in the form of its trifluoroacetic salt.

To obtain the base of the compound, 25.0 g trifluoroacetic salt (50 mmoles) is subjected to vigorous stirring with 200 ml normal soda and 200 ml ethyl acetate. The mixture is decanted, the soda extracted with 50 ml ethyl acetate and the ethylacetate washed with 50 ml saturated aqueous sodium chloride solution. After drying and evaporation, the product yield is 19.0 g (97%).

TLC: AcOEt/MeOH 90/10 Rf=0.30 and 0.40 (2 spots corresponding to the 2 isomers)

| NMR: | | | |
|---|---|---|---|
| 8.72 ppm | d | 1 proton | CN—NH—CO |
| 7.60–6.90 ppm | m | 8 protons | aromatics |
| 5.42 ppm | m | 8 protons | CH—NH—CO |
| 4.40 ppm | m | 1 proton | CH2N |
| 3.95 ppm | m | 1 proton | CH2N |
| 3.60–3.0 ppm | m | 3 protons | CO—CH—NH, CH2Ar |
| 2.0–1.20 ppm | m | 3 protons | CHCH2 |
| 1.70 ppm | s | 2 protons | NH2 |
| 0.95 ppm | m | 6 protons | (CH3)2 |

IR: 3350, 2950, 1660, 1600, 1440, 1380, 1240 cm$^{-1}$.

Stage 2c: Separation of the optical isomers of N-(-L-leucyl-)-amino-4-phenyl-6-tetrahydro-1,2,3,4-pyrrolo[3,2,1-j,k] benzodiazepin-[1,4]-one-3.

A flash chromatography apparatus is prepared with 400 g silica in a column 5 cm in diameter. 19.0 g of the base obtained in the preceding stage are dissolved in the ethylacetate and eluted in succession with pure ethylacetate (2.5 l), ethylacetate containing 5% methanol (2.5 l), ethylacetate containing 10% methanol (2.5 l) and ethylacetate containing 20% methanol (2.5 l); the results are examined on silica plate, combined and then the fractions of identical quality evaporated, yielding:

isomer A: 11.5 g.

isomer mixture: 0.4 g.

isomer B: 11.5 g.

Separation yield: 96% (48% of each isomer)

isomer A: TLC: AcOET/MeOH 90/10 Rf=0.5.

[α]D= −0.1 °5 (c=1.0; CH2Cl2).

isomer B: TLC: AcOEt/MeOH 90/10 Rf=0.3.

[α]D= +56 °3 (c=1.0; CH2Cl2).

Stage 2d: preparation of phenyl-6-N-[-(N-phenyl-thioureido)-L-leucyl-]-amino-4(R)-tetrahydro-1,2,3,4-pyrrolo[3,2,1-j,k]benzodiazepin [1,4]-one-3.

Formula (X): A=—(CH2)2—; R9=H; R10=R34=phenyl; R11=H; R31=isobutyl; isomer B 4.05 g phenylisothiocyanate (30 mmoles) are added dropwise to a stirred solution of 11.7 g isomer B from the previous stage (30 mmoles) in methylene chloride. The progress of the reaction is followed on plate. The solvent is evaporated after 1 hour. The residue (15.5 g) is redissolved in methylene chloride containing 10% ethylacetate and chromatographed on silica in ethylacetate-enriched methylene chloride. Evaporation yields 15 g (95%) product.

TLC: CH2Cl2/ethylacetate 85/15 Rf=0.4.

Stage 2e: (+)-(4R)-amino-4-phenyl-6-tetrahydro-1,2,3,4-pyrrolo [3,2,1-j,k] benzodiazepin-[1,4]-one-3.

Formula II: A=—(CH2)2-; R9=H; R10=phenyl; dextrorotatory isomer 5.8 g (30 mmoles) phenyl-6-N-(-(N-phenyl-thioureido-)-L-leucyl-)-amino-4-tetrahydro-1,2,3,4-pyrrolo[3,2,1-j,k] benzodiazepin-[1,4]-one-3, obtained from stage 2d above, is dissolved in 200 ml trifluoroacetic acid at normal temperature under constant stirring. Heating is carried out for 1 hour at 40° C. followed by evaporation. Methylene chloride is boiled off several times to eliminate the excess trifluoroacetic acid. Chromatographs are recorded on silica, eluting with ethylacetate progressively enriched with methanol. The yield is 8 g (68%) white needles of trifluoroacetate from (+)-(4R)-amino-4-phenyl-6-tetrahydro-1,2,3,4-pyrrolo[3,2,1-j,k] benzodiazepin [1,4]-one-3.

TLC: CH2Cl2/ethylacetate 85/15 Rf=0.4.

| NMR: | | | |
|---|---|---|---|
| 7.60–6.90 ppm | m | 8 protons | aromatics |
| 4.65 ppm | m | 1 proton | CH2N |
| 4.45 ppm | s | 1 proton | CHNH3 |
| 3.90 ppm | m | 1 proton | CH2N |
| 3.50–2.90 ppm | m | 5 protons | NH3, CH2Ar |

Stage 2f: (product of Example 2) 46 (4R)-N-(keto-3-phenyl-6-tetrahydro-1,2,3,4-pyrrolo[3,2,1-j,k]benzodiazepine[1,4]-yl-4)-N'-(methyl-3-phenyl-)-urea.

This compound is prepared from optically active (4R)-amino-4-phenyl-6-tetrahydro-1,2,3,4-pyrrolo[3,2,1-j,k] benzodiazepin-[1,4]-one-3, operating in the same way as for the preparation of the compound in Example 1 in stage (1c), based on 5.54 g amine (20 mmoles) and 2.66 g methyl-3-phenylisocyanate (20 mmoles). After purification by flash chromatography on a silica column, elution with a mixture of increasing polarity of acetone in methylene chloride yields 6.5 g (79% of the compound.

F=182° C. [α]D= +76° (c=1.0; ethanol).

TLC: CH2Cl2/acetone 95/5 Rf=0.25.

Example 3:
N-[keto-3-(fluoro-2-phenyl)-6-tetrahydro-1,2,3,4-pyrrolo[3,2,1-j,k]benzodiazepine-[1,4]-yl-4-]-N'-[(methyl-3-)-phenyl-]-urea Formula (I): A=—(CH2)2—; R9=H;
R10=fluoro-2-phenyl; R11=H; R12=O; R13=NH;
Ar=methyl-3-phenyl.

STage 3a: (Fluoro-2-benzoyl)-7-indoline.

43.03 g (361 mmoles) indoline are dissolved in 360 ml tetrachlorethane in a reactor fitted with central stirring of a cooling medium including calcium chloride protection, an immersion thermometer, a nitrogen input and a bromine ampoule to maintain the pressure. After cooling in a glacial bath 46.75 g (399 mmoles) boron trichloride in solution in 180 ml tetrachloroethane are added in dropwise fashion. 84.0 g (694 mmoles) fluoro-2-benzonitrile are added, followed by 52.2 g (399 mmoles) aluminium trichloride. The mixture is heated for 8 h at 150° C. After cooling, hydrolysis is effected with 325 ml 4N hydrochloric acid. After further heating for 20 minutes at 80° C. to complete hydrolysis, the mixture is cooled and the insoluble element filtered off, followed by rinsing with ether and drying. The precipitate is redissolved in methylene chloride and alkalized with soda. Washing of the organic solution with a concentrated sodium chloride solution is followed by drying on sodium sulphate. A yield of 63.0 g yellow resin (72%) is obtained after filtration and evaporation.

TLC: Ch2Cl2 Rf=0.5

| NMR: | | | | |
|---|---|---|---|---|
| 7.50–7.0 ppm | m | 7 protons | | aromatics |
| 6.40 ppm | m | 1 proton | | NH |
| 3.80 ppm | t | 2 protons | J = 9 Hz | CH2N |
| 3.0 ppm | t | 2 protons | J = 9 Hz | CH2Ar |

Stage 3b: N-bromoacetyl-(fluoro-2-benzoyl-)-7-indoline.

117.0 g (485 mmoles) of product from stage (a) are suspended in 2.5 l ether in a reactor fitted with central stirring of a cooling medium including calcium chloride protection, an immersion thermometer, a nitrogen input and a bromine ampoule to maintain the pressure. After cooling to 20° C., 41 ml (485 mmoles) pyridine followed by 91.6 g (582 mmoles) bromoacetyl chloride are added in dropwise fashion. The temperature is allowed to return to ambient temperature and stirring carried out for 20 hj. 2 l water is added under stirring and the insoluble element filtered off. The product is rinsed with water then with hexane and dried, followed by recrystallization in ethylacetate. The yield is 120.0 g (61%) N-bromoacetyl(fluoro-2-benzoyl-)-7-indoline.
MP=136° C.

TLC: CH2Cl2/acetone 95/5 Rf=0.25

| NMR: | | | |
|---|---|---|---|
| 7.90–6.90 ppm | m | 7 protons | aromatics |
| 4.20 ppm | t | 2 protons | CN2 N |
| 3.76 ppm | s | 2 protons | COCH2Br |
| 3.20 ppm | t | 2 protons | CH2Ar |

IR: 1660, 1610, 1450, 1390, 1210, 1100, 1050, 745 cm$^{-1}$.

Stage 3c: (Fluoro-2-phenyl)-6-tetrahydro-1,2,3,4-pyrrolo[3,2,1-j,k] benzodiazepin-[1,4]-one-3.

Formula (III): A=—(CH2)2—; R9=H;
R10=fluoro-2-phenyl 1 l tetrahydrofuran and 570 ml methanol anhydride are poured out in a reactor fitted with central stirring of a cooling medium including calcium chloride protection, an immersion thermometer, a nitrogen input and a bromine ampoule to maintain the pressure. After cooling to −30° C., 320 ml liquid ammonia is added. 114.0 g (314 mmoles) product from the preceding stage is then added gradually and left to stand under stirring until the following day, without external cooling. The whole product dissolves slowly. Evaporation to dryness is carried out after 20 h, followed by washing with water. The yield is 140.0 g gross product, which is chromatographed on silica, eluting with methylene chloride progressively enriched with acetone. The yield is 70.0 g (fluoro-2-phenyl)-6-tetrahydro-1,2,3-pyrrolo[3,2,1-j,k]benzodiazepin-[1,4]-one-3 (79%).
MP=148° C.

TLC: CH2Cl2/acetone 95/5 Rf=0.6.

| NMR: | | | |
|---|---|---|---|
| 7.60–6.90 ppm | m | 7 protons | aromatics |
| 4.40 ppm | s | 2 protons | COCH2N |
| 4.30 ppm | t | 2 protons | CH2N |
| 3.20 ppm | t | 2 protons | CH2Ar |

IR: 1665, 1600, 1445, 1395, 1345, 1210, 740 cm$^{-1}$.

Stage 3d: Hydroximino-4-(fluoro-2-phenyl)-6-tetrahydro-1,2,3,4-pyrrolo[3,2,1-j,k] benzodiazepin-[1,4]-one-3. Formula (IV): A=—(CH2)2—; R9=H; R10=fluoro-2-phenyl.

Following the same procedure as in Example 1, Stage 1a, 70.0 g (249 mmoles) of the product from the preceding stage yields 67.0 g (87%) of a yellow solid
MP=218° C. (decomposition)

TLC: CH2Cl2/acetone 95/5 Rf=0.29

| NMR (hexadeuterized DMSO): | | | |
|---|---|---|---|
| 7.80–6.95 ppm | m | 7 protons | aromatics |
| 4.25 ppm | t | 2 protons | CH2N |
| 3.40 ppm | s | 3 protons | NOH, H2O |
| 3.20 ppm | t | 2 protons | CH2Ar |

IR: 3450, 3120, 3000, 2700, 1620, 1600, 1340, 1300, 1000, 740 cm$^{-1}$.

Stage 3e: amino-4-(fluoro-2-phenyl)-6-tetrahydro-1,2,3,4-pyrrolo [3,2,1-j,k]benzodiazepin-[1,4]-one-3.

Formula (II): A=—(CH2)2-; R9=H;
R10=fluoro-2phenyl

1st method

Operating in the same way as in Example 2, Stage 1b, 2nd method, 30 g (969 mmoles) pf the product from the preceding stage yields 28 g (98%) of a foamed product, which is used directly in the following reactions.

TLC: CH2Cl2/MeOH 95/5 Rf=0.54.

| NMR: | | | |
|---|---|---|---|
| 7.70–6.90 ppm | m | 7 protons | aromatics |
| 4.45 ppm | m | 1 proton | CH2N |
| 4.3 ppm | s | 1 proton | CHNH2 |
| 3.90 ppm | m | 1 proton | CH2N |

| NMR: | | | |
|---|---|---|---|
| 3.50–3.10 ppm | m | 2 protons | CH2Ar |
| 3.20 ppm | s | 2 protons | NH2 |

IR: 3400, 1680, 1580, 1440, 1200, 740 cm$^{-1}$.

2nd method 5.8 g (168 nmoles) of product from Stage (d) are suspended in methanol under nitrogen atmosphere and 3.99 g (168 mmoles) nickel chloride hexahydrate addd. Cooling to −20° C. is followed by the addition of 1.2 g (336 mmoles) sodium borohydride in small quantities. The temperature rises immediately with the formation of a black precipitate. Stirring is carried out at −20° C. for 30 minutes followed by evaporation to dryness. The product is redissolved in concentrated hydrochloric acid, filtered and alkalized with a concentrated ammonia solution in the presence of methylene chloride. Evaporation yields 6.8 g gross product which is chromatographed on silica, eluting with methylene chloride progressively enriched with acetone. The yield is 2.8 g (48%) of a foamed product identical with that obtained by the first method.

Stage 3f

This compound is prepared form amino-4-(fluoro-2-phenyl)-6-tetrahydro-1,2,3,4-pyrrolo∂3,2,1-j,k] benzodiazepin-[1,4]-one-3 in the same way as in Example 1, stage 1c. 5.0 g (17 mmoles) amine and 2.26 g (17 mmoles) methyl-3-phenyl-isocyanate, after purification by flash chromatography on a silica column, the elution agent used being a mixture of increasing polarity of acetone in methylene chloride, yields 4.0 g (55%) compound in the form of a white solid. MP=190° C.

TLC: CH2CH12/acetone 90/10 Rf=0.30.

| NMR: | | | |
|---|---|---|---|
| 9.0 ppm | d | 1 proton | Ar—NH—CO |
| 7.70–6.70 ppm | m | 12 protons | ArH, NH |
| 5.20 ppm | d | 1 proton | CO—CH—N |
| 4.70–4.30 ppm | m | 1 proton | CH2—N |
| 4.20–3.70 ppm | m | 1 proton | CH2—N |
| 3.60–2.8- ppm | m | 2 protons | CH2Ar |
| 2.25 ppm | s | 3 protons | CH3Ar |

IR: 3200, 3050, 3000, 1685, 1640, 1600, 1560, 1520, 1465, 1440, 1430, 1380, 1340, 1285, 1210 and 1190 cm$^{-1}$.

Example 4:

N-[keto-3-chloro-8-(fluoro-2-phenyl-)-6-tetrahydro-1,2,3,4-pyrrolo [3,2,1-j-k]benzodiazepin-[1,4]-yl-4]-N′-[(methyl-3-)-phenyl-]-urea Formula (I): A=—(CH2)2—; R9=chloro-8; R10=fluoro-2-phenyl; R11=H; R12=O; R13=NH; Ar=methyl-3-phenyl Stage 4a: Chloro-5-(fluoro-2-benzoyl-)-7-indoline.

44.0 g (182 mmoles) (fluoro-2-benzoyl)-7-indoline, as prepared in stage 3a, Example 1, and 800 ml methylene chloride are poured out in a reactor fitted with central stirring of a cooling medium including calcium chloride protection, an immersion thermometer, a nitrogen input and a bromine ampoule to maintain the pressure. 27.94 g (182 mmoles) N-chlorosuccinimide are added gradually and stirred overnight at ambient temperature. The product is washed with saturated sodium bicarbonate solution, then with water, dried and evaporated. Chromatography is carried out on silica, eluting with methylene chloride. The yield is 42.0 g (84%) product in the form of a foamed product having no clearly defined melting pont.

TLC: CH2Cl2 Rf=0.7

| NMR: | | | |
|---|---|---|---|
| 7.60–7.00 ppm | m | 6 protons | aromatics |
| 6.30 ppm | m | 1 proton | NH, |
| 3.85 ppm | m | 2 protons | CH2N |
| 3.10 ppm | m | 2 protons | CH2Ar |

Stage 4b: N-bromoacetyl-chloro-b 5-(fluoro-2-benzoyl)-7-indoline.

55.0 g (199 mmoles) product from the preceding stage are treated as in Stage 3b, Example 1, with 34.46 g (219 mmoles) bromacetyal bromide. The yield is 60.0 g (76%) product.

TLC: CH2Cl2 Rf=0.25

| NMR: | | | |
|---|---|---|---|
| 7.90–6.80 ppm | m | 6 protons | aromatics |
| 4.25 ppm | t | 2 protons | CH2N |
| 3.80 ppm | s | 2 protons | CH2Br |
| 3.20 ppm | t | 2 protons | CH2Ar |

Stage 4c: Chloro-8-(fluoro-2-phenyl)-6-tetrahydro1,2,3,4-pyrrolo [3,2,1-j,k]benzodiazepin-[1,4]-one-3.

Formula (III): A=—(CH2)2—; R9=chloro-8; R10=fluoro-2-phenyl

Operating as in Example 3, Stage 3c, 90.0 g (226 mmoles) product from the preceding stage yields after chromatography in an acetone-enriched methylene chloride gradient 46.3 g (65%) product. MP=148° C.

| NMR: | | | |
|---|---|---|---|
| 7.60–7.00 ppm | m | 6 protons | aromatics |
| 4.45 ppm | s | 2 protons | CO—CH2—N |
| 4.32 ppm | t | 2 protons | CH2N |
| 4.20 ppm | t | 2 protons | CH2Ar |

IR: 1660, 1550, 1370, 1340, 1224, 880, 800, 745 cm$^{-1}$.

Stage 4d: Chloro-8-(fluoro-2-phenyl)-6-hydroximino-4-tetrahydro-1,2,3,4-pyrrolo[3,2,1-j,k] benzodiazepin [1,4]-one-3.

Formula (IV): A=—(CH2)2—; R9=chloro-8; R10=fluoro-2-phenyl

Operating in the same fashion as in Example 1, Stage 1a, 45 g (143 mmoles) of product from the preceding stage yields 33 g (67%) of a yellow solid. MP=264° C. (decomposition). TLC: CH2Cl2/acetone 90/10 Rf=0.27.

| NMR: | | | |
|---|---|---|---|
| 7.85–7.0 ppm | m | 6 protons | aromatics |
| 4.32 ppm | t | 2 protons | CH2N |
| 3.48 ppm | s | 1 proton | NOH |
| 3.28 ppm | t | 2 protons | CH2Ar |

IR: 3300, 1655, 1625, 1580, 1445, 1370, 1340, 1220, 1160, 1020, 850, 740 cm$^{-1}$.

Stage 4e: Amino-4-chloro-8-(fluoro-2-phenyl)-6-tetrahydro-1,2,3,4-pyrrolo[3,2,1-j,k]benzodiazepin-[1,4]-one-3.

Formula (II): A=—(CH2)2—; R9=chloro-8; R10=fluoro-2-phenyl.

Operating in the same manner as in Example 1, Stage 1b, 2nd method, 30 g (870 mmoles) of product from the preceding stage yield 28 g (98%) of a foamed product which is used directly in the subsequent reactions.
TLC: CH2Cl2/MeOH 95/5 Rf=0.55

| NMR: | | | | |
|---|---|---|---|---|
| 7.70–6.95 | ppm | m | 6 protons | aromatics |
| 4.60 | ppm | m | 1 proton | CH2N |
| 4.40 | ppm | s | 1 proton | CH—NH2 |
| 4.0 | ppm | m | 1 proton | CH2N |
| 3.23 | ppm | m | 2 protons | CH2Ar |
| 2.50 | ppm | s | 2 protons | NH2 |

IR: 3350, 1670, 1610, 1580, 1440, 1335, 1220, 860, 790, 750 cm$^{-1}$.

Stage 4f: (product of the example)

This compound is prepared from mamino-4-chloro-8-(fluoro-2-phenyl)-6-tetrahydro-1,2,3,4-pyrrolo[3,2,1-j,k benzodiazepin-[1,4]-one-3 in the same way as in Example 1, using 4.0 g (12 mmoles) of the amine obtained in the perceding stage and 1.88 g (12 mmoles) methyl-3-phenylisocyanate. After purification by flash chromatography on a silica column, the elution agent used being a mixture of increasing polarity of methanol in methylene chloride, the yield is 3.5 g (62%) of the compound in solid form.
MP=256° C. (decomposition).
TLC: CH2Cl2/acetone 90/10 Rf=0.25

| NMR: | | | | |
|---|---|---|---|---|
| 9.0 | ppm | d | 1 proton | Ar—NH—CO |
| 7.70–6.7– | ppm | m | 11 protons | ArH, NH |
| 5.25 | ppm | d | 1 proton | CO—CH—N |
| 4.70–4.30 | ppm | m | 1 proton | CH2—N |
| 4.20–3.80 | ppm | m | 1 proton | CH2—N |
| 3.60–2.80 | ppm | m | 2 protons | CH2Ar |
| 2.25 | ppm | s | 3 protons | Ch3Ar |

IR: 3320, 1690, 1640, 1590, 1560, 1480, 1340, 1230, 1130, 750 cm$^{-1}$.

Example 5:
(5R,S)-N-(keto-4-phenyl-7-hexahydro-1,2,3,3a,4,5-pyrido [3,2,1-j,k]benzodiazepine-[1,4]-yl-5)-N'-(methyl-3-phenyl-)-urea.

Formula (I): A=—(CH2)3—; R9=H; R10=phenyl; R11=H; R12=O; R13=NH; Ar=methyl-3-phenyl.

Stage 5a: Hydroximino-5-phenyl-7-hexahydro-1,2,3,3a,4,5-pyrido[3,2,1-j,k]benzodiazepin-[1,4-one-4.

Formula (IV): A=—(CH2)3-; R9=H; R10=phenyl

The compound is prepared in the same way as in Example 1, Stage 1a, from 26.9 g phenyl-7-hexahydro-1,2,3,3a,4,5-pyrido[3,2,1-j,k]benzodiazepine-1.4-one-4 (97 mmoles). After chromatography in methylene chloride progressively enriched with acetone, 24.3 g of a solid compound is isolated.
MP=195° C.

TLC: CH2Cl2/acetone 90/10 Rf=0.3; CH2Cl2/methanol 95/5 Rf=0.35.

| NMR: | | | | |
|---|---|---|---|---|
| 9.20 | ppm | s | 1 proton | NOH |
| 7.60–6.80 | ppm | m | 8 protons | aromatics |
| 4.60 | ppm | m | 1 proton | CH2N |
| 3.20 | ppm | m | 1 proton | CH2N |
| 2.95 | ppm | m | 2 protons | CH2Ar |
| 2.00 | ppm | m | 2 protons | CH2—CH2—CH2 |

IR: 3200, 1685, 1600, 1320, 1260, 1130, 1115 cm$^{-1}$

Stage 5b: Amino-5-phenyl-7-hexahdyro-1,2,3,3a,4,5-pyrido[3,2,1-j,k]-benzodiazepin-1,4-one-4.

Formula (II): A=—(CH2)3—; R9=H; R10=phenyl.

The compound is prepared as in Example 1, Stage 1b, 2nd method from 28.8 g of the compound prepared in the above state (94 mmoles). After chromatography in methylene chloride progressively enriched with methanol, a foam product is isolated (22.0 g) having no clearly defined melting point, which is used directly in the subsequent reactions.
TLC: CH2CH12/acetone 90/10 Rf=0.10; CH2Cl2/methanol 95/5 Rf=0.25.

| NMR: | | | | |
|---|---|---|---|---|
| 7.70–7.00 | ppm | m | 8 protons | aromatics |
| 5.00 | ppm | m | 2 protons | CH2N, CHNH2 |
| 3.30 | ppm | m | 1 proton | CH2N |
| 2.90 | ppm | m | 2 protons | CH2Ar |
| 2.62 | ppm | s | 2 protons | NH2 |
| 2.40–1.70 | ppm | m | 2 protons | CH2—CH2—CH2 |

IR: 1670, 1590, 1440, 1300, 1270 cm$^{-1}$.

Stage 5c: (5R,S)-N-(keto-4-phenyl-7-hexahydro-1,2,3,3a,4,5-pyrido[3,2,1-j,k]benzodiazepine-[1,4]-yl-4)-N'-(methyl-3-phenyl-)-urea.

This compound is prepared from racemic (5R,S)-amino-5-phenyl-7-hexahydro-1,2,3,3a,4,5-pyrido[3,2,1-j,k]benzodiazepin-[1,4]-one-4, prepared in Stage 5b above, in the same way as the compound in Stage 1c, Example 1, using 4.37 g amine (15 mmoles) and 1.99 g methyl-3-phenylisocyanate (15 mmoles). After filtration of the precipitate and washing with methylene chloride, the yield is 5.15 g (81%) of the compound. MP=195° C.
TLC: CH2Cl2/acetone 95/5 Rf=0.25; CH2Cl2MeOH 95/5 Rf=0.75.

| NMR: | | | | |
|---|---|---|---|---|
| 9.03 | ppm | s | 1 proton | CO—NH—Ar |
| 7.70–6.60 | ppm | m | 13 protons | ArH, NH |
| 5.30 | ppm | d | 1 proton | Co—CH—N |
| 4.60–4.15 | ppm | m | 1 proton | Ch2N |
| 3.40–3.05 | ppm | m | 1 proton | Ch2N |
| 3.05–2.6 | ppm | m | 2 protons | CCH2Ar |
| 2.3 | ppm | s | 3 protons | CH3Ar |
| 2.30–1.6 | ppm | m | 2 protons | CH2CH2CH2 |

IR: 3300, 1670, 1640, 1610, 1590, 1550, 1490, 1440, 1370, 1290, 1200 cm$^{-1}$.

Example 6:
(5S)-N-(keto-4-phenyl-7-hexahydro-1,2,3,3a,4,5-pyrido[3,2,1-j,k]benzodiazepine[1,4-yl-4)-N'-(methyl-3-phenyl-)-urea.

Formula (I): A=—(CH2)3—; R9=H; R10=phenyl; R11p32 H; R12p32 O; R13=NH; Ar=methyl-3-phenyl; levorotatory isomer.

Stage 6a: Phenyl-7-[N-tetriobutyloxy-carbonyl-L-leucyl-)-amino]-5-hexahydro-1,2,3,3a,4,5-pyrido[3,2,1-j,k]benzodiazepin-1,4-one-4.. Formula (VIII): A=—(CH2)3—; R9=H; R10=phenyl; R31=isobutyl; R32=tetriobutyloxycarbonyl.

47.77 g tertiobutyloxycarbonyl-L-leucine hydrate (192 mmoles) followed by 21.32 g N-methylmorpholine (23.2 ml or 211 mmoles) are dissolved in 60 ml dichloromethane and 120 mlDMF. The mixture is allowed to stand under stirring for 5 min at ambient temperature, then cooled to −20° C. 27.4 ml isobutyl chloroformate (211 mmoles) are then added and stirred for 30 minutes at −20° C. 67.0 g amino-5-phenyl7-hexahydro-1,2,3,3a,4,5-pyrido[3,2,1-j,k]benzodiazepin-1,4-one-4 (230 mmoles) in solution in 600 ml at −20° C. and for 48 h at ambient temperature. After evaporation, the residue is chromatographed on silica in dichloromethane containing 5% acetone. A 99.6 g (94%) yield of purified product is obtained.

TLC: Ch2Cl2/acetone 95/5 Rf=0.60

| NMR: | | | | |
|---|---|---|---|---|
| 8.00–7.8 | ppm | d | 1 proton | NH |
| 7.70–7.0 | ppm | m | 9 protons | ArH, NH |
| 5.60–5.4 | ppm | d | 1 proton | COCHN |
| 5.30–5.1 | ppm | m | 1 proton | COCHN |
| 4.70–4.15 | ppm | m | 1 proton | CH2—N |
| 3.40–3.0 | ppm | m | 1 proton | CH2—N |
| 3.00–2.7 | ppm | m | 2 protons | CH2Ar |
| 2.50–1.6 | ppm | m | 5 protons | CCH2C, CHCH2 |
| 1.50–1.3 | ppm | s | 9 protons | CO—OC(CH3)3 |
| 1.00–0.8 | ppm | d | 6 protons | CH(CH3)2 |

Stage 5b: (N-L-leucyl-)-amino-5-phenyl-7-hexahydro-1,2,3,3a,4,5-pyrido[3,2,1-j,k]benzodiazepin-1,4-one-4.

Formula (IX): A=—(CH2)3—; R9=H; R10=phenyl; R31=isobutyl

The tertiobutyloxycarbonyl group is eliminated in the same way as in Example 2, Stage 2b. Using 100.0 g product from the preceding stage (198 mmoles) 76.2 g (95%) pure amine is obtained after neutralization of the salt and chromatography of the base.

Stage 6c: Enantiomers of (N-L-leucyl-)-amino-5-phenyl-7-hexahydro-1,2,3,3a,4,5-pyrido[3,2,1-j,k]benzodiazepin-1,4-one-4.

Using the perceding product, as for Example 2, Stage c, chromatography on 3 kg silica in ethylacetate, and eluting with ethylacetate followed by ethylacetate containing 5% methanol then 10% methanol, yields 36.4 g (90 mmoles) levorotatory derivative [α]D=−155 °7 (c=1%, ethanol) and 30.8 g (0.076 mole) of the dextrorotatory derivative [α]D=+119°7 (c=1%, ethanol).

Stage 6d: [N-(N-phenyl-thioureido-)-L-leucyl-]-amino-5-phenyl-7-hexahydro-1,2,3,3a,4,5-pyrido[3,2,1-j,k]benzodiazepin-1,4-one-4.

Formula (X): A=—(CH2)3—; R9=H; R10=R34=phenyl; R31=isobutyl

Using the same procedure as in Example 2 Stage 2d, 36.4 g levorotatory amine (90 mmoles) from the preceding stage yields 39.2 g product (81%).

| NMR | | | | |
|---|---|---|---|---|
| 8.45–8.35 | ppm | s | 1 proton | CH—NH—CO |
| 7.90–7.70 | ppm | d | 1 proton | NH |
| 7.60–7.00 | ppm | m | 13 protons | ArH |
| 7.00–6.80 | ppm | d | 1 proton | NH |
| 5.50–5.20 | ppm | d + m | 2 protons | NCHCOM NCHCO |
| 4.65–4.30 | ppm | m | 1 proton | CH2N |
| 3.40–3.00 | ppm | m | 1 proton | Ch2N |
| 3.00–2.70 | ppm | m | 2 protons | CH2Ar |
| 2.20–1.40 | ppm | m | 5 protons | CCH2C, CHCH2 |
| 1.05–0.80 | ppm | m | 6 protons | (CH3)2 |

Stage 6e: (−)-amino-(5S)-phenyl-7-hexahydro-1,2,3,3a,4,5-pyrido[3,2,1-j,k]benzodiazepin-1,4-one-4.

Formula (II): A=—(CH2)3—; R9=H; R10=phenyl; levorotatory isomer.

Using the same procedure as in Example 2 Stage 2e, 40 g (74 mmoles) of the product of stage 6d, yield, after purification and neutralization, 16.8 g (78%) compound.

[α]D=−271° (c=1%, ethanol).

| NMR: | | | | |
|---|---|---|---|---|
| 7.70–6.90 | ppm | m | 8 protons | ArH |
| 4.70–4.30 | ppm | m | 1 proton | CH2N |
| 4.45 | ppm | s | 1 proton | NCHCO |
| 3.40–3.00 | ppm | m | 1 proton | CH2N |
| 3.00–2.70 | ppm | m | 2 protons | Ch2Ar |
| 2.70–2.50 | ppm | s | 2 protons | NH2 |
| 2.40–1.70 | ppm | m | 2 protons | CH2CH2CH2 |

Stage 6f: (product of the example) (5S)-N-(keto-4-phenyl-7-hexahydro-1,2,3,3a,4,5-pyrido[3,2,1-j,k]benzodiazepin [1,4]-yl-4)-N'-(methyl-3-phenyl-)-urea.

150 ml dichloromethane and 8.8 g of the levorototory amine prepared above (23.3 mmoles) are introduced into a 250 ml flask, fitted with a nitrogen input, calcium chloride protection and a magnetic stirrer. 3.1 g methyl-3-phenyl isocyanate (23.3 mmoles) are then added rapidly at ambient temperature and the mixture allowed to stand for 1 hour under stirring. Evaporation followed by chromatography on silica, eluting with acetone-enriched (95/5)dichloromethane, yields 9.0 g solid. MP=190° C.

TLC: CH2Cl2/acetone 95/5 Rf=0.35.

[α]D=−98° (c=1%, ethanol)

| NMR: | | | | |
|---|---|---|---|---|
| 7.95 | ppm | s | 1 proton | CO—NH—Ar |
| 7.70–6.70 | ppm | m | 13 protons | ArH, NH |
| 5.60–5.80 | ppm | d | 1 proton | CO—CH—N |
| 4.70–4.30 | ppm | m | 1 proton | CH2—N |
| 3.45–3.05 | ppm | m | 1 proton | CH2—N |
| 3.0–2.80 | ppm | m | 2 protons | C—CH2—Ar |
| 2.30 | ppm | s | 3 protons | CH3 |
| 2.30–1.70 | ppm | m | 2 protons | CH2CH2CH2 |

Example 7:
(+)-(5R)-N-(keto-4-phenyl-7-hexahdyro-1,2,3,3a,4,5-pyrido[3,2,1-j,k]benzodiazepine[1,4]-yl-5)-N'-(methyl-3-phenyl-)-urea.

Formula (I): A=—(CH2)3—; R9=H; R10=phenyl; R11=H; R12=O; R13=NH; Ar=methyl-3-phenyl; dextrorotatory isomer Stage 7a: [N-(N-phenyl-thioureido-)-L-leucyl-]-amino-5-phenyl-7-hexahydro-1,2,3,3a,4,5-pyrido[3,2,1-j,k]benzodiazepin-1,4-one-4.

Formula (X): A=—(CH2)3—; R9=H; R10p32 R34=phenyl; R31=isobutyl

The procedure described in Example 2, Stage 2d, is used on 30.8 g dextrorotatory amine from Example 6 Stage 6c (76 mmoles). The yield is 39.0 g products (95%).

| NMR: | | | | |
|---|---|---|---|---|
| 8.45–8.35 | ppm | s | 1 proton | CH—NH—CO |
| 7.90–7.70 | ppm | d | 1 proton | NH |
| 7.60–7.00 | ppm | m | 14 protons | ArH, NH |
| 5.50–5.20 | ppm | d + m | 2 protons | NCHCO, NCHCO |
| 4.60–4.20 | ppm | m | 1 proton | CH2N |
| 3.40–2.95 | ppm | m | 1 proton | CH2N |
| 3.00–2.70 | ppm | m | 2 protons | CH2Ar |
| 2.20–a.40 | ppm | m | 5 protons | CCH2C, CHCH2 |
| 1.05–0.80 | ppm | m | 6 protons | (CH3)2 |

Stage 7f: Preparation of (+)-amino-(5R)-phenyl-7-hexahydro-1,2,3,3a,4,5-pyrido[3,2,1-j,k]benzodiazepin-1,4-one-4.

Formula (II): A=—(CH2)3—; R9=H; R10=phenyl; R14=O, dextrorotatory isomer

Using the same procedure as in Example 2, Stage 2, on 41.0 g (76 mmoles product of Stage 7a yields, after purification and neutralization, 14.2 g (68%)
[αD[=+257° (c=1%, ethanol).

| NMR: | | | | |
|---|---|---|---|---|
| 7.70–6.90 | ppm | m | 8 protons | ArH |
| 4.70–4.30 | ppm | m | 1 proton | CH2N |
| 4.45 | ppm | s | 1 proton | NCHCO |
| 3.40–3.00 | ppm | m | 1 proton | CH2N |
| 3.00–2.70 | ppm | m | 2 protons | CH2Ar |
| 2.70–2.50 | ppm | m | 2 protons | NH2 |
| 2.40–1.70 | ppm | m | 2 protons | CH2CH2CH2 |

Stage 7c: (+)-(5R)-N-(keto-4-phenyl-7-hexahdyro-1,2,3,3a,4,5-pyrido[3,2,1-j,k]benzodiazepin[1,4]-yl-5)-N'-(methyl-3-phenyl-)-urea.

Using the same procedure as in Example 2 Stage 2f, 8.8 g (30.2 mmoles) product of Stage 7b yields, after purification, 11.5 g (90%) of a solid which melts at 180° C.
[α]D=+94° (c=1% ethanol).
TLC: CH2Cl2/acetone 95/5 Rf=0.35.

| NMR: | | | | |
|---|---|---|---|---|
| 7.90 | ppm | s | 1 proton | CO—NH—Ar |
| 7.70–6.70 | ppm | m | 13 protons | ArH, NH |
| 5.80–5.60 | ppm | d | 1 proton | CO—CH—N |
| 4.70–4.30 | ppm | m | 1 proton | CH2—N |
| 3.45–3.05 | ppm | m | 1 proton | CH2—N |

| NMR: | | | | |
|---|---|---|---|---|
| 3.0–2.70 | ppm | m | 2 protons | CH2—Ar |
| 2.30 | ppm | s | 3 protons | CH3 |
| 2.30–1.70 | ppm | m | 2 protons | CH2CH2CH2 |

Example 8:
(5R,S)-N-(keto-4-phenyl-7-hexahydro-1,2,3,3a,4,5-pyrido[3,2,1-j,k]benzodiazepine-[1,4]-yl-5)-N'-(nitro-4-phenyl-)-urea Formula (I): A=—(CH2)3—; R9p32 HI R10=phenyl; R11=H; R12=O; R13=NH; Ar=—nitro-4-phenyl This compound is prepared from racemic (5R,S)-amino-5-phenyl-7-hexahydro-1,3,4,4a,4,5-pyrido[3,2,1-j,k]benzodiazepin-[1,4]-one-4 in the same manner as for preparation of the compound of Example 1.

The user of 3.60 g amine (12 mmoles) and 2.02 g nitro-4-phenylisocyanate (12 mmoles) yields 3.7 g (70%) compound. MP>290° C.
TLC: CH2Cl2/acetone 90/10 Rf=0.55.

| NMR: | | | | |
|---|---|---|---|---|
| 9.85 | ppm | s | 1 proton | CONHAr |
| 8.2 | ppm | d | 1 proton | NH |
| 8.00–7.00 | ppm | m | 12 protons | ArH |
| 5.30 | ppm | d | 1 proton | COCHN |
| 4.60–4.20 | ppm | m | 1 proton | CH2N |
| 3.50–3.10 | ppm | m | 1 proton | Ch2N |
| 3.10–2.60 | ppm | m | 2 protons | CCH2Ar |
| 2.40–1.60 | ppm | m | 2 protons | CCH2C |

Ir: 3300, 2280, 1660, 1610, 1560, 1490, 1440, 1380, 1320, 1200, 1160, 820 cm$^{-1}$.

Example 9:
(5R,S)-N-(keto-4-phenyl-7-hexahydro-1,2,3,3a,4,5-pyrido[3,2,1-j,k]benzodiazepine-[1,4-yl-5)-N'-(fluoro-4-nitro-3-phenyl-)-urea Formula (I): A=—(CH2)3—; R9=H; R10=phenyl; R11=H; R12=O; R13=NH; Ar=fluoro-4-nitro-3-phenyl This compound is prepared from racemic (5R,S)-amino-5-phenyl-7-hexahydro-1,2,3,3a,4,5-pyrido[3,2,1-j,k]benzodiazepin-[1,4]-one-4 in the same way as in Example 1.

Using 4.0 g amine (13.7 mmoles) an d2.50 g fluoro-4-nitro-3-phenylisocyanate (13.7 mmoles) yields 6.0 g (92%) compound in the form of a white solid. MP>290° C.
TLC: CH2Cl2/acetone 95/5 Rf=0.15.

| NMR: | | | | |
|---|---|---|---|---|
| 8.20 | ppm | d | 1 proton | CONHAr |
| 7.90 | ppm | s | 1 proton | CNHCO |
| 7.70–7.00 | ppm | m | 11 protons | ArH |
| 5.55 | ppm | d | 1 proton | COCHN |
| 4.50–4.30 | ppm | m | 1 proton | CH2N |
| 3.30–3.10 | ppm | m | 1 proton | CH2N |
| 3.00–2.65 | ppm | m | 2 protons | CCH2Ar |
| 2.20–1.70 | ppm | m | 2 protons | CCH2C |

IR: 3300, 3050, 1640, 1600, 1500, 1440, 1300, 1260, 1200, 1160, 810, 800 cm$^{-1}$.

Example 10:
(5R,S)-N-(keto-4-phenyl-7-hexahydro-1,2,3,3a,4,5-pyrido[3,2,1-j-k]benzodiazepine-[1,4]-yl-5)-N'-(bromo-4-phenyl-)-thiourea Formula (I): A=—(CH2)3—; R9=H; R10=phenyl; R11=H; R12=S; R13=NH; Ar=bromo-4-phenyl 5.1 g (4R,S)-amino-5-phenyl-7-hexahydro-1,2,3,3a,4,5-pyrido[3,2,1-j,k]-benzodiazepin-[1,4]-one-4 (17.5 mmoles) are dissolved in 50 ml methylene chloride after which 3.75 g bromo-4-phenyl isothiocyanate (17.5 mmoles) are added. The solvent is evaporated after 45 min stirring at ambient temperature. Chromatography is carried out on a silica column in a mixture of methylene chloride containing 5 vol % acetone. After evaporation, the residue is redissolved in ethanol. The solution is filtered and evaporated. The yield obtained is 4.3 g (50%) compound. MP=215° C.

TLC=CH2Cl2/acetone 95/5 Rf=0.40.

| NMR: | | | | |
|---|---|---|---|---|
| 9.2–8.5 | ppm | s | 1 proton | CO—NH—Ar |
| 7.8–7.1 | ppm | m | 13 protons | ArH, NH |
| 5.85 | ppm | | 1 proton | CSCHN |
| 4.6–4.2 | ppm | m | 1 proton | CH2N |
| 3.4–3.1 | ppm | m | 1 proton | CH2N |
| 3–2.7 | ppm | m | 2 protons | CH2Ar |
| 2.2–1.6 | ppm | s | 2 protons | CH2CH2CH2 |

IR; 3350, 1660, 1560, 1480, 1380, 1380, 1230, 1170 cm$^{-1}$.

Example 11:
(5R,S)-N-(keto-4-phenyl-7-hexahydro-1,2,3,3a,4,5-pyrido[3,2,1-j,k]-benzodiazepin [1,4]-yl-5)-N'-(methyl-3-phenyl-)-thiourea Formula (I): A=—(CH2)3—; R9=H; R10=phenyl; R11=H; R12=S; R13=NH; Ar=methyl-3-phentl This product is prepared in the manner described in the previous example from 4.0 g (4R,S)-amino-5-phenyl-7-hexahydro-1,2,3,3a,4,5-pyrido[3,2,1-j,k]-benzodiazepin [1,4]-one-4 (13.7 mmoles) and 2.05 g methyl-3-phenyl isothiocyanate (13.7 mmoles). The product is purified by flash chromatography, the elution agent used being dichloromethane containing 2.5% acetone. The yield in this case is 4.7 g of the required product (78.5%). MP=175° C.

TLC: CH2Cl2/acetone 95/5 Rf=035.

| NMR: | | | | |
|---|---|---|---|---|
| 10.2 | ppm | s | 1 proton | NH |
| 8.8 | ppm | d | 1 proton | NH |
| 7.7–6.7 | ppm | m | 12 protons | ArH |
| 6–5.9 | ppm | d | 1 proton | Ch2N |
| 3.4–3.1 | ppm | m | 1 proton | CH2N |
| 3.1–2.7 | ppm | m | 2 protons | CCH2Ar |
| 2.3 | ppm | s | 3 protons | CH3 |
| 2.2–1.7 | ppm | m | 2 protons | CH2CH2CH2 |

IR: 3350, 3150, 2950, 1660, 1580, 1540, 1440, 1280, 1250, 1180 cm$^{-1}$.

Example 12:
(5R,S)-N-(keto-4-phenyl-7-hexahydro-1,2,3,3a,4,5-pyrido[3,2,1-j,k]-benzodiazepin [1,4]-yl-5)-N'-(methyl-2-phenyl-)-urea Formula (I): A=—(CH2)3—; R9=H; R10=phenyl; R11=H; R12=o; R13=NH; Ar=methyl-2-phenyl This compound is prepared from racemic (5R,S)-amino-5-phenyl-7-hexahydro-1,2,3,3a,4,5-pyrido[3,2,1-j,k]-benzodiazepin [1,4]-one-4 in the same way as for the preparation of the compound of Example 1.

Using 2.91 g amine (10 mmoles) and 1.33 g methyl-2-phenylisocyanate (10 moles)* yields 3.00 g (75%) of the compound in the form of a solid.

* Presumably (10 mmoles). Translator's Note.

MP=190° C.

TLC: CH2Cl1/acetone 90/10 Rf=0.50.

| NMR: | | | | |
|---|---|---|---|---|
| 8.70–7.00 | ppm | m | 14 protons | ArH, NHCONH |
| 5.53 | ppm | d | 1 proton | COCHN |
| 4.60–4.20 | ppm | m | 1 proton | CH2N |
| 3.30–2.90 | ppm | m | 1 proton | CH2N |
| 2.90–2.60 | ppm | m | 2 protons | CCH2Ar |
| 2.20–1.60 | ppm | m | 2 protons | CCH2C |
| 2.10 | ppm | s | 3 protons | CH3Ar |

IR: 3300, 2920, 1670, 1640, 1580, 1515, 1480, 1470, 1290, 1160, 730 cm$^{-1}$.

Example 13:
(5R,S)-N-(keto-4-phenyl-7-hexahydro-1,2,3,3a,4,5-pyrido[3,2,1-j,k]-benzodiazepine-[1,4]-yl-5)-N'-(methyl-4-phenyl-)-urea Formula (I): A=—(CH2)3—; R9=H; R10=phenyl; R11=H; R12=O; R13=NH; Ar=methyl-4-phenyl This compound is prepared from racemic (5R,S)-amino-5-phenyl-7-hexahydro-1,2,3,3a,4,5-pyrido[3,2,1-j,k]-benzodiazepin [1,4]-one-4 in the same way as for preparation of the compound of Example 1.

Using 2.91 g amine (10 mmoles) and 1.33 g methyl-4-phenylisocyanate (10 mmoles) yields 3.10 g (73%) compound in the form of a solid.

MP=280° C.

TLC: CH2Cl2/acetone 90/10 Rf=0.46.
CH2Cl2/MeOH 95/5 Rf=0.65.

| NMR: | | | | |
|---|---|---|---|---|
| 9.00 ppm | s | 1 proton | CONHAr |
| 7.60–6.90 ppm | m | 13 prolons | ArH,NH |
| 5.30 ppm | d | 1 proton | COCHN |
| 4.60–4.10 ppm | m | 1 proton | CH2N |
| 3.40–3.05 ppm | m | 1 proton | CH2N |
| 3.05–2.60 ppm | m | 2 protons | CCH2Ar |
| 2.40–1.60 ppm | m | 2 protons | CCH2C |
| 2.25 ppm | s | 3 protons | ArCH3 |

IR: 3400, 3050, 2700, 2500, 1600, 1540, 1490, 1440, 1365, 1300, 1180, 800 cm$^{-1}$.

Example 14:
(5R,S)-N-(keto-4-phenyl-7-hexahydro-1,2,3,3a,4,5-pyrido[3,2,1-j,k]-benzodiazepin[1,40-yl-5)-N'-(trifluoromethyl-2-phenyl-)-urea Formula (I): A=—(CH2)3—; R9=H; R10=phenyl; R11=H; R12=O; R13=NH; Ar-trifluoromethyl-2-phenyl This compound is prepared from racemic (5R,S)-amino-5-phenyl-7-hexahydro-1,2,3,3a,4,5-pyrido[3,2,1-j,k]-benzodiazepin [1,4]-one-4 in the same way as for preparation of the compound of Example 1.

2.91 g amine (10 mmoles) and 1.87 g trifluoromethyl-2-phenylisocyanate (10 mmoles) yields 3.6 (75%) compound. MP>290°C.

TLC:CH2Cl2/acetone 95/5 Rf=0.30. CH2Cl2/MeOH 95/5 Rf=0.50.

| NMR: | | | |
|---|---|---|---|
| 7.95–7.05 ppm | m | 14 protons | ArH,NHCONH |
| 5.27 ppm | d | 1 proton | COCHN |
| 4.55–4.15 ppm | m | 1 proton | CH2N |
| 3.55–3.05 ppm | m | 1 proton | CH2N |
| 3.05–2.70 ppm | m | 2 protons | CCH2Ar |
| 2.30–1.60 ppm | m | 2 protons | CCH2C |

IR: 3350, 3050, 1660, 1600, 1520, 1440, 1370, 1310, 1200, 1150, 1100, 740 cm⁻¹.

Example 15:
(5R,S)-N-(keto-4-phenyl-7-hexahydro-1,2,3,3a,4,5-pyrido[3,2,1-j,k]-benzodiazepine-[1,40-yl-5-yl-5)-N'-(naphthyl-1-phenyl-)-urea Formula (I): A=—(CH2)3—; R9=H; R10=phenyl; R11=H; R12=O; R13=NH; Ar=naphthyl-1-

This compound is prepared from racemic ((5R,S)-amino-5-phenyl-7-hexahydro-1,2,3,3a,4,5-pyrido[3,2,1-j,k]-benzodiazepin-[1,4]-one-4 in the same way as for the preparation of Example 1.

Using 2.91 g amine (10 mmoles) and 1.69 g naphthyl-1-isocyanate (10 mmoles) yields 3.9 g (85%) compound. MP=190° C.

TLC: CH2Cl2/acetone 95/5 Rf=0.15. CH2Cl2/MeOH 95/5 Rf=0.35.

| NMR: | | | |
|---|---|---|---|
| 9.20 ppm | s | 2 protons | CONHAr |
| 8.40–7.10 ppm | m | 15 protons | ArH,NH |
| 5.40 ppm | d | 1 proton | COCHN |
| 4.60–4.10 ppm | m | 1 proton | CH2N |
| 3.40–3.05 ppm | m | 1 proton | CH2N |
| 3.05–2.6- ppm | m | 2 protons | CCH2Ar |
| 2.40–1.60 ppm | m | 2 protons | CCH2 |

IR: 3300, 3030, 3000, 1670, 1640, 1540, 1440, 1380, 1200, 760 cm⁻¹.

Example 16:
(5R,S)-N-(keto-4-phenyl-7-hexahydro-1,2,3,3a,4,5-pyrido[3,2,1-j,k]-benzodiazepine[1,4]-yl-5)-N'-(bromo-2-phenyl-)-thiourea Formula (I): A=—(CH2)3—; R9=H; R10=phenyl; R11=H; R12=S; R13=NH; Ar=bromo-2-phenyl This product is prepared in the same way as in Example 23 from 3.00 g (4R,S)-amino-5phenyl-7-hexahydro-1,2,3,3a,4,5-pyrido[3,2,1-j,k]-benzodiazepin-[1,4]-one-4- (10.3 mmoles) and 2.20 g bromo-2-phenyl isothiocyanate (10.3 mmoles). The product is purified by flash chromatography, using dichloromethane with a 2.5% acetone content as elution agent. The yield thus obtained is 4.07 g of the required product (77%). MP=180° C.

TLC: Ch2Cl2/acetone 95/5 Rf=0.5. CH2Cl2/MeOH 95.5 Rf=0.85.

| NMR: | | | |
|---|---|---|---|
| 8.20–6.90 ppm | m | 14 protons | ArH, NHCSNH |
| 6.05 ppm | d | 1 proton | COCHN |
| 4.70–4.30 ppm | m | 1 proton | CH2N |
| 3.40–3.00 ppm | m | 1 proton | CH2N |
| 3.05–2.70 ppm | m | 2 protons | CCH2Ar |
| 2.40–1.70 ppm | m | 2 protons | CH2CH2CH2 |

IR: 3300, 2900, 1660, 1580, 1520, 1440, 1280 cm⁻¹.

Example 17:
(4R,S)-N-(keto-3-phenyl-6-tetrahydro-1,2,3,4-pyrrolo[3,2,1-j,k]-benzodiazepine[1,4]-yl-4)-N'-(bromo-4-phenyl-)-thiourea Formula (I): A=—(CH2)2-R9=H; R10=phenyl; R11=H; R12=S; R13=NH; Ar=bromo-4-phenyl This compound is prepared from the (4R,S)-amino-4-phenyl-6-tetrahydro-1,2,3,3a,4,5-pyrrolo[3,2,1-j,k]-benzodiazepin-[1,4]-one-3, prepared in Stage 1b of Example 1(2nd method) and using the same procedure as for the compound of Stage 1c. 4.0 g amine (14.4 mmoles) and 3.4 g chloro-4-phenylisothiocyanate (14.4 mmoles), after purification by chromatography on silica in acetone-enriched methylene chloride, yields 5.0 g (83%) compound in solid form. MP=160° C.

TLC: Ch2Cl2/acetone 80/20 Rf=0.6.

| NMR: | | | |
|---|---|---|---|
| 8.70 ppm | m | 1 proton | NH |
| 8.50 ppm | d | 1 proton | NH |
| 7.40–7.00 ppm | m | 12 protons | ArH |
| 5.95 ppm | d | 1 proton | CHN |
| 4.80–4.30 ppm | m | 1 proton | CH2 |
| 4.30–3.65 ppm | m | 1 proton | CH2 |
| 3.60–2.90 ppm | m | 2 protons | CCH2 |

IR: 3300, 1675, 1600, 1505, 1490, 1470, 1395, 1240 c⁻¹.

Example 18:
(4R,S)-N-(keto-3-phenyl-6-tetrahydro-1,2,3,4-pyrrolo-[3,2,1-j,k]-benzodiazepine[1,4]-yl-4)-N'-(bromo-3-phenyl-)-thiourea Formula (I): A=—(CH2)2—; R9=H; R10=phenyl; R11=H; R12=S; R13=NH; Ar=bromo-3-phenyl This compound is prepared from (4R,S)-amino-4-phenyl-6-tetrahydro-1,2,3,4-pyrrolo[3,2,1-j,k]-benzodiazepin-[1,4]-yl-4)-one-3. Using 6.0 g amine (21.6 mmoles) and 4.69 g bromo-3-phenylisothiocyanate (14.4 mmoles) yields, after chromatography on silica using acetone-enriched methylene chloride as elution agent, 7.3 g (69%) solid compound. MP=135° C.

TLC: CH2Cl2/acetone 97/3 Rf=0.30.

| NMR: | | | |
|---|---|---|---|
| 8.70 ppm | m | 1 proton | NH |
| 8.45 ppm | d | 1 proton | NH |
| 7.70–7.00 ppm | m | 12 protons | ArH |

-continued

| NMR: | | | |
|---|---|---|---|
| 6.0 ppm | d | 1 proton | CHN |
| 4.70–4.40 ppm | m | 1 proton | CH2 |
| 4.10–3.60 ppm | m | 1 proton | CH2 |
| 3.60–2.80 ppm | m | 2 protons | CCH2 |

IR: 3300, 1670, 1510, 1485, 1470, 1240, 1170, 700 cm$^{-1}$.

EXAMPLE 19:
(4R,S)-N-(keto-3-phenyl-6-tetrahydro-1,2,3,4-pyrrolo[3,2,1-j,k]-benzodiazepine[1,4]-yl-4)-N'-(bromo-4-phenyl-)-thiourea Formula (I): A=—(CH2)2—; R9=H; R10=CH/4-C6H4; R11=H; R12=S; R13=NH; Ar=bromo-4-phenyl Stage 19a: Transformation of a compound (III) into compound (IV).

The compound is prepared from 134 g (1.125 moles) indolinea nd 253 g (2.16 moles) methyl-4-benzonitrile. The yield is 259 g (93%) methyl-4-benzoyl-7-indoline. MP=106° C.

| NMR: | | | |
|---|---|---|---|
| 7.70–7.10 ppm | m | 7 protons | ArH |
| 3.70 ppm | t | 2 protons | CH2 |
| 3.10 ppm | t | 2 protons | CH2 |
| 2.40 ppm | s | 3 protons | ArCH3 |

IR: 3350, 1620, 1600, 1500, 1460, 1390, 1290, 1260, 1010, 740 cm$^{-1}$.

Stage 19b: N-bromoacetyl-(methyl-4-benzoyl)-7-indoline, prepared from 249 g (1.05 mole) of the product prepared in Stage 34a above, is treated as described in Stage 3b, yielding 265 g (70%) solid compound.

TLC: CH2Cl2/acetone 95/5 Rf=0.70.

| NMR: | | | |
|---|---|---|---|
| 7.85–7.10 ppm | m | 7 protons | ArH |
| 4.45–4.15 ppm | t | 2 protons | CH2 |
| 3.75 ppm | s | 2 protons | BrCH2CO |
| 3.35–3.00 ppm | t | 2 protons | CH2 |
| 2.40 ppm | s | 3 protons | ArCH3 |

IR: 1660, 1600, 1580, 1450, 1400, 1280, 990, 870, 830, 740 cm$^{-1}$.

Stage 19c: (Methyl-4-phenyl-)-6-tetrahydro-1,2,3,4-pyrrolo[3,2,1-j,k]benzodiazepin[1,4]-one 3.

Formula (III): A=—(CH2)2—; R9=H; R10=CH34—C6H4

Using the same procedure as described in Example 3, 266 g (743 mmoles) product of the above stage yields 143.5 g (70%) solid product. MP=203° C.
TLC: CH2Cl2/acetone 95/5 Rf=0.3

| NMR: | | | |
|---|---|---|---|
| 7.50–6.90 ppm | m | 7 protons | ArH |
| 4.40–4.15 ppm | t | 2 protons | CH2 |
| 4.35 ppm | d | 2 protons | COCH2N |
| 3.30–3.05 ppm | t | 2 protons | CH2 |
| 3.40 ppm | s | 3 protons | ArCH3 |

IR: 1670, 1600, 1450, 1385, 1345, 1305, 1040, 820, 755 cm$^{-1}$.

Stage 19d: Hydroximino-4-(methyl-4-phenyl-)-6-tetrahydro-1,2,3,4-pyrrolo[3,2,1-j,k]benzodiazepin[1,4]-one-3. Formula (IV): A=—(CH2)2—; R9=H; R10=CH34—C6H4.

Based on 143 g (517 mmoles) of the product of the above stage, the yield is 117 g (82%) product. MP=202° C. (decomposition.
TLC: Ch2Cl2/acetone 95/5 Rf=0.24.

| NMR: | | | |
|---|---|---|---|
| 7.70–7.00 ppm | m | 7 protons | ArH |
| 4.40–4.10 ppm | m | 2 protons | CH2 |
| 3.85 ppm | s | 1 proton | |
| 3.40–3.00 ppm | m | 2 protons | CH2 |
| 2.40 ppm | s | 3 protons | ArCH3 |

IR: 3200, 1680, 1600, 1440, 1385, 1345, 1300, 1230, 1010, 920, 800, 740 cm$^{-1}$.

Stage 19e: Amino4-(methyl-4-phenyl-)-6-tetrahydro-1,2,3,4-pyrrolo[3,2,1-j,k]benzodiazepin[1,4]-one-3.

Formula (II): A=—(CH2)2—; R9=H; R10=CH34—C6H4;

Following the same procedure as in Stage 1b, 2nd method, 35 g (12 mmoles of the compound of Stage 34d yields, after chromatography, 24.5 g (70%) of the required compound in the solid form.
MP=115 C.
TLC: CH2Cl2/acetone 80/20 Rf=0.20.

| NMR: | | | |
|---|---|---|---|
| 7.60–7.00 ppm | m | 7 protons | ArH |
| 4.80–4.50 ppm | m | 2 protons | CH2 |
| 4.35 ppm | s | 1 proton | CHN |
| 4.20–3.70 ppm | m | 2 protons | CH2 |
| 3.60–3.00 ppm | m | 2 protons | CH2 |
| 2.75 ppm | s | 2 protons | |
| 2.38 ppm | s | 3 protons | CH3 |

IR: 3350, 2900, 1680, 1600, 1445, 1390, 1240, 820, 760, 735 cm$^{-1}$.

Stage 19f: The same procedure is followed as in Example 1, STage 1c, using 6 g (20.6 mmoles) of the product of the preceding stage and 44 g (20.6 mmoles) bromo-4-phenyl isocyanate. 7 g solid product (67%) is obtained after purification by chromatography on silica in acetone-enriched methylele chloride.
MP=150° C.
TLC: Ch2Cl1/acetone 97/30 Rf=0.46.

| NMR: | | | |
|---|---|---|---|
| 8.71 ppm | s | 1 proton | NH |
| 8.15 ppm | d | 1 proton | NH |
| 7.60–7.00 ppm | m | 11 protons | ArH |
| 5.95 ppm | d | 1 proton | NCHCO |
| 4.80–4.40 ppm | m | 1 proton | CH2 |
| 4.10–3.60 ppm | m | 1 proton | CH2 |
| 3.60–2.90 ppm | m | 2 protons | CH2 |
| 2.38 ppm | s | 3 protons | CH3 |

IR: 3300, 1675, 1600, 1510, 1490, 1300, 1240, 1060, 1000, 820, 740 cm$^{-1}$.

Example 20:
(5R,S)-N-(keto-4-phenyl-7-hexahydro-1,2,3,3a,4,5-pyrido[3,2,1-j,k]benzodiazepine[1,4]-yl-5)-N'-(pyridyl-3-)-urea Formula (I): A=—(CH2)3—; R9=H; R10=C6H6; R11=H; R12=O; R13=NH; Ar=pyridyl-3

1.5 g (16 mmoles) amino-3-pyridine are dissolved in 80 ml methylene chloride. 2.6 g (16 mmoles) N,N'-carbonyldiimidazole is added and the mixture stirred for 3 h at ambient temperature. After cooling to 0° C., a solution of 4.6 g (16 mmoles) of the amine obtained in Stage 5b, Example 5, in 40 ml methylene chloride are added. Filtration of the precipitate thus formed is followed by chromatography on silica in methanol-enriched methylene chloride. The yield obtained is 4.25 g (65%) solid product. MP=280° C.

TLC: CH2Cl2/methanol 90/10 Rf=0.5.

| NMR: | | | |
|---|---|---|---|
| 9.3 ppm | s | 1 proton | NH |
| 8.6–7.0 ppm | m | 13 protons | ArH,NH |
| 5.3 ppm | d | 1 proton | COCHN |
| 4.55–4.10 ppm | m | 1 proton | CH2 |
| 3.40–3.0 ppm | m | 1 proton | CH2 |
| 3.0–2.15 ppm | m | 2 protons | CH2 |
| 2.3–1.5 ppm | m | 2 protons | CH2 |

IR: 3320, 1670, 1640, 1595, 1540, 1475, 1300, 1200, 820, 690 cm$^{-1}$.

Example 21:
(5R,S)-N-(keto-4-phenyl-7-hexahydro-1,2,3,3a,4,5-pyrido[3,2,1-j,k]benzodiazepine[1,4]-yl-5)-N'-(pyridnyl-4-)-urea Formula (I): A=—(CH2)3—; R9=H; R10=C6H5; R11=H; R12=O; R13=NH; Ar=pyridyl-4

The same procedure is followed as in the above example, based on 1.7 g (13.7 mmoles) amino-4-pyridine, 4.6 g (13.7 mmoles) amine obtained from Stage 5g, Example 5, and 2.43 g (15 mmoles) N,N'-carbonyldiimidazole. After chromatography on silica in acetone-enriched methylene chloride, 4.9 g (87%) solid product is isolated, melting above 280° C. with decomposition.

TLC: CH2 Cl1/acetone 95/5 Rf=0.35.

| NMR: | | | |
|---|---|---|---|
| 9.52 ppm | s | 1 proton | NH |
| 8.32 ppm | d | 1 proton | NH |
| 7.90–6.80 ppm | m | 12 protons | ArH |
| 5.3 ppm | d | 1 proton | COCHN |
| 4.55–4.10 ppm | m | 1 proton | CH2 |
| 3.50–3.05 ppm | m | 1 proton | CH2 |
| 3.0–2.5 ppm | m | 2 protons | CH2 |
| 2.4–1.5 ppm | m | 2 protons | CH2 |

IR: 3300, 1660, 1590, 1520, 1380, 1200, 830, 740, 690 cm$^{-1}$.

Example 22:
(5R,S)-N-(keto-4-phenyl-7-hexahydro-1,2,3,3a,4,5-pyrido[3,2,1-j,k]benzodiazepine[1,4]-yl-50-N'-(bromo-3-phenyl-)-thiourea Formula (I): A=—(CH2)3—; R9=H; R10=C6H5; R11=H; R12=S; R13=NH; Ar=bromo-3-phenyl The same procedure is used as in Example 5, based on 5.8 g (20 mmoles) of the amine obtained in Stage 5b and 4.28 g (20 mmoles) bromo-3-phenyl isothiocyanate. After chromatography on silica in acetone-enriched methylene chloride, this yields 5.0 g (50%) solid product. MP=185° C.

TLC: CH2Cl2/acetone 95/5 Rf=0.60.

| NMR: | | | |
|---|---|---|---|
| 10.4 ppm | s | 1 proton | NH |
| 9.0 ppm | s | 1 proton | NH |
| 8.2–7.0 ppm | m | 12 protons | ArH |
| 5.9 ppm | d | 1 proton | CHCHN |
| 4.60–4.20 ppm | m | 1 proton | CH2 |
| 3.50–3.10 ppm | m | 1 proton | CH2 |
| 3.0–2.60 ppm | m | 2 protons | CH2 |
| 2.3–1.6 ppm | m | 2 protons | CH2 |

IR: 3300, 1670, 1645, 1600, 1540, 1505, 1475, 1370, 1300, 1200, 1160, 790, 680 cm$^{-1}$.

Example 23:
(5R,S)-N-(keto-4-phenyl-7-hexahydro-1,2,3,3a,4,5-pyrido[3,2,1-j,k]benzodiazepine[1,4]-yl-5)-N'-(quinolinyl-3-)-urea Formula (I): A=—CH2)3-; R9=H; R10=C6H6; R11=H; R12=O; R13=NH; Ar=quinolinyl-3

The same procedure is followed as in the example above, based on 1.73 g (12 mmoles) amino-3-quinoline, 3.5 g (12 mmoles) amine obtained from Stage 5b, Example 5, and 1.944 g (12 mmoles) N,N'-carbonyldiimidazole. After chromatography on silica in acetone-enriched methylene chloride, 4.4 g (80%) solid product is isolated, melting above 280° C. with decomposition.

TLC: CH2Cl2/methanol 90/10 Rf=0.55.

| NMR: | | | |
|---|---|---|---|
| 9.65 ppm | s | 1 proton | NH |
| 9.0–7.0 ppm | m | 15 protons | ArH,NH |
| 5.4 ppm | d | 1 proton | COCHN |
| 4.65–4.20 ppm | m | 1 proton | CH2 |
| 3.50–3.10 ppm | m | 1 proton | CH2 |
| 3.10–2.60 ppm | m | 2 protons | CH2 |
| 2.4–1.6 ppm | m | 2 protons | CH2 |

IR: 3350, 3050, 1660, 1580, 1500, 1480, 1340, 1250, 1200, 880, 780, 740, 695 cm$^{-1}$.

Example 24:
(5S)-N-(keto-4-phenyl-7-hexahydro-1,2,3,3a,4,5-pyrido[3,2,1-j,k]benzodiazepine[1,4]-yl-5)-N'-(bromo-4-phenyl-)-thiourea Formula (I): A=—(CH2)3-; R9=H; R10=C6H5; R11=H; R12=S; R13=NH; R14=O; Ar-bromo-4-phenyl;levorotatory isomer (Iaq)

Following the same procedure as in Example 10, 5.2 g (17.8 mmoles) of the amine obtained in Stage 6e, and 3.8 g (17.8 mmoles) bromo-4-phenyl isocycanate are chromatographed on silica in acetone-enriched methylene chloride. The yield is 7.7 g (86%) crystals. MP=200° C.

[α]D=—93° C. (EtOH c=1%).

TLC: CH2Cl2/acetone 95/5 Rf=0.40.

| NMR: | | | |
|---|---|---|---|
| 8.9 ppm | s | 1 proton | NH |
| 8.2 ppm | d | 1 proton | NH |
| 7.70–7.0 ppm | m | 12 protons | ArH |
| 6.0 ppm | d | 1 proton | COCHN |

-continued

| NMR: | | | |
|---|---|---|---|
| 4.55–4.20 ppm | m | 1 proton | CH2 |
| 3.40–3.0 ppm | m | 1 proton | CH2 |
| 3.0–2.50 ppm | m | 2 protons | CH2 |
| 2.3–1.6 ppm | m | 2 protons | CH2 |

IR: 3300, 1660, 1580, 1500, 1440, 1380, 1160 cm$^{-1}$.

Example 25:
(5S)-N-(keto-4-phenyl-7-hexahydro-1,2,3,3a,4,5-pyrido[3,2,1-j,k]benzodiazepine[1,4]-yl-4)-N'-(methyl-4-phenyl-)-urea Formula (I): A=—(CH2)3—; R9=H; R10; C6H5; R11=H; R12=O; R13=NH; Ar-methyl-4-phenyl; levorotatory isomer Using the same procedure as in Example 1, 2.6 g (9 mmoles) of the amine obtained in Stage 6e and 1.19 g (9 mmoles) methyl-4-phenyl isocyanate are chromatographed on silica in acetone-enriched methylene chloride, yielding 2.7 g (71%) crystals. MP=190° C. [=]D=−155° (CH2Cl2 c=1%).

TLC: CH2Cl2/acetone 90/10 Rf=0.46.

| NMR: | | | |
|---|---|---|---|
| 9.0 ppm | s | 1 proton | NH |
| 7.60–6.90 ppm | m | 13 protons | ArH,NH |
| 5.30 ppm | d | 1 proton | COCHN |
| 4.60–4.10 ppm | m | 1 proton | CH2 |
| 3.40–3.05 ppm | m | 1 proton | CH2 |
| 3.05–2.60 ppm | m | 2 protons | CH2 |
| 2.35 ppm | s | 3 protons | CH3 |
| 2.4–1.6 ppm | m | 2 protons | CH2 |

IR: 3300, 2900, 1675, 1640, 1600, 1540, 1500, 1440, 1380, 1200, 1160, 790, 740, 700 cm$^{-1}$.

Example 26:
(5S)-N-(keto-4-phenyl-7-hexahydro-1,2,3,3a,4,5-pyrido[3,2,1-j,k]benzodiazepine[1,4]-yl-4)-N'-(bromo-4-phenyl-)-thiourea Formula (I): —(CH2)3—; R9'H; R10=C7H5; R11=H; R12=S; r13=NH; Ar=bromo-4-phenyl; dextrorotatory isomer.

Using the same procedures as in Example 10, 4.75 g (16 mmoles) of the amine obtained in Stage 7b and 3.49 g (16 mmoles) bromo-4-phenyl isocyanate are chromatographed on silica in acetone-enriched methylene chloride, yielding 7.0 g (86.5%) crystals. MP=200° C. [α]D=+95° (EtOH c=1%).

TLC: CH2Cl2/acetone 95/5 Rf=0.40.

| NMR: | | | |
|---|---|---|---|
| 8.85 ppm | s | 1 proton | NH |
| 8.15 ppm | d | 1 proton | NH |
| 7.65–6.90 ppm | m | 12 protons | ArH |
| 6.0 ppm | d | 1 proton | COCHN |
| 4.50–4.25 ppm | m | 1 proton | CH2 |
| 3.35–3.0 ppm | m | 1 proton | CH2 |
| 3.0–2.60 ppm | m | 2 protons | CH2 |
| 2.4–1.6 ppm | m | 2 protons | CH2 |

IR: 3300, 1660, 1580, 1500, 1440, 1380, 1160 cm$^{-1}$.

Example 27:
(5S)-N-(keto-4-phenyl-7-hexahydro-1,2,3,3a,4,5-pyrido[3,2,1-j,k]benzodiazepine]1,4]-yl-4)-N'-(methyl-4-phenyl-)-urea.

Formula (I): A=—(CH2)3—; R9=H; R10=C6H5; R11=H; R12=O; R13=NH; Ar; methyl-4-phenyl; dextrorotatory isomer.

Using the same procedure as in Example 13, 2.9 g (10 mmoles) of the amine obtained in Stage 7b and 1.33 g (10 mmoles) methyl-4-phenyl isocycanate are chromatographed on silica in acetone-enriched methylene chloride, yielding 2.1 g (50%) crystals. MP=190° C. [α]D'+157° (CH2Cl2 c=1%).

TLC: CH2Cl2/acetone 90/10 Rf=0.46.

| NMR: | | | |
|---|---|---|---|
| 7.80–6.85 | ppm | m | 14 protons | ArH, 2NH |
| 5.60 | ppm | d | 1 proton | COCHN |
| 4.70–4.25 | ppm | m | 1 proton | CH2 |
| 3.40–3.0 | ppm | m | 1 proton | CH2 |
| 3.0–2.50 | ppm | m | 2 protons | CH2 |
| 2.25 | ppm | s | 3 protons | CH3 |
| 2.35–1.60 | ppm | m | 2 protons | CH2 |

IR: 3300, 2900, 1660, 1600, 1540, 1500, 1440, 1370, 1200, 1160, 810, 740, 700 cm$^{-1}$.

Example 28:
(5R,S)-N-(keto-4-(methyl-4-phenyl-7-hexahydro-1,2,3,3a,4,5-pyrido[3,2,1-j,k]benzodiazepine[1,4]-yl-5)-N'-)bromo-3-phenyl-)-thiourea.

Formula (I): A=—(CH2)3—; R9=H; R10=methyl-4-phenyl; R11=H; R12=S; R13=NH; Ar=bromo-3-phenyl.

Stage 28a. Transformation of a compound of formula (III) into a compound of formula (IV).

This compound is prepared from 25.8 g (194 mmoles) tetrahydro-1,2,3,4-quinoline and 45.5 g (388 mmoles) methyl-4-benzonitrile, using the same procedure as in stage 3a. The yield obtained is 25.4 g (52%) (methyl-4-benzoyl-)-8-tetrahydro 1,2,3,4-quinoline. MP=94° C.

TLC: CH2Cl2Rf=0.70.

Cyclohexane/AcOEt 90/10 Rf=0.30.

| NMR: | | | |
|---|---|---|---|
| 8.7 | ppm | s | 1 proton | NH |
| 7.7–6.95 | ppm | m | 7 protons | ArH |
| 3.65–3.30 | ppm | m | 2 protons | Ch2N |
| 2.70–3.0 | ppm | m | 2 protons | CH2 |
| 2.45 | ppm | s | 3 protons | CH3 |
| 2.20–1.60 | ppm | m | 2 protons | CH2 |

IR: 3300, 2900, 1660, 1580, 1470, 1380, 1240, 1160, 820, 750 cm$^{-1}$.

Stage 28b. N-bromoacetyl-(methyl-4-benzoyl-)-8-tetrahydro-1,2,3,4-quinoline.

Using the procedure described in Stage 3b, Example 3, 12.5 g (50 mmoles) of the product of Stage 28a above yields 8.5 g (46%) crystals.

The highly unstable product is used immediately in the following reaction.

Stage 28c; Keto-4-hexahydro-1,2,3,3a,4,5-(methyl-4-phenyl-)-7-pyrido[3,2,1-j,k]benzodiazepine[1,4].

Using the same procedure as in Stage 3c, Example 3, 10 g (26.8 mmoles) yields 4 g (50%) crystals.

TLC: CH2Cl2/acetone 95/5 Rf=0.1. CH2Cl2/MeOH 90/10 Rf=0.7.

| NMR: | | | | |
|---|---|---|---|---|
| 7.5–6.8 | ppm | m | 7 protons | ArH |
| 4.78–4.65-3,78,3,65 | | AB | 2 protons | CO—CH2—N |
| 4.60–4.25 | ppm | m | 1 proton | CH2N |
| 3.25–2.90 | ppm | m | 1 proton | CH2N |
| 2.90–2.15 | ppm | m | 2 protons | CH2 |
| 2.30 | ppm | s | 3 protons | CH3Ar |
| 2.25–1.60 | ppm | m | 2 protons | CH2 |

Stage 28d. Hydroximino-5-hexahydro-1,2,3,4a,4,5-(methyl-4-phenyl-)-7-pyrido[3,2,1-j,k]benzodiazepine[1,4].

Formula (IV): A=—(CH2)3—; R9=H; R10=methyl-4-phenyl.

In the same way as in Example 1, Stage 1a, 138 g (476 mmoles) of the product of the above stage, after chromatography in acetone-enriched methylene chloride, yields 118 g (80%) solid compound. MP=170° C.
TLD: CH2Cl2/MeOH 90/10 Rf=0.70.

| NMR: | | | | |
|---|---|---|---|---|
| 7.80–6.10 | ppm | m | 7 protons | ArH |
| 4.5 | ppm | m | 1 proton | OH |
| 3.0–2.70 | ppm | m | 2 protons | CH2 |
| 2.70–2.20 | ppm | m | 2 protons | CH2 |
| 2.38 | ppm | s | 3 protons | CH3Ar |
| 2.20–1.70 | ppm | m | 2 protons | CH2 |

Stage 28e. Amino-5-keto-4-hexahydro-1,2,3,3a,4,5-(methyl-4-phenyl-)-7-pyrido[3,2,1-j,k]benzodiazepine[1,4].

Formula (II): A=—(CH2)3—; R9=H; R10=methyl-4-phenyl.

The same procedure is used as in Example 1, Stage 2nd method, based on 35 g (109 mmoles) of the compound obtained in the above stage. After chromatography on silica in methanol-enriched methylene chloride; 24.0 g (80%) foam product are isolated, having no clear melting point, which is used immediately in the following reactions. MP about 110° C.
TLC: CH2Cl2/MeOH 90/10 Rf=0.60.

| NMR: | | | | |
|---|---|---|---|---|
| 7.80–6.90 | ppm | m | 7 protons | ArH |
| 4.70–4.25 | ppm | m | 2 protons | CHN, CH2N |
| 3.45–3.0 | ppm | m | 1 proton | CH2N |
| 3.0–2.45 | ppm | m | 2 protons | CH2 |
| 2.35 | ppm | s | 3 protons | CH3Ar |
| 2.95–1.50 | ppm | m | 2 protons | CH2 |

Stage 28f; (product of the example)
Using the same procedure as in Example 22, based on 3.07 g (10 mmoles) of the amine obtained in the preceding stage and 2.14 g (10 mmoles) bromo-3-phenyl isothiocyanate yields 4 g (77%) crystals. MP=170° C.
TLC: CH2Cl2/acetone 95/5 Rf=0.55

| NMR: | | | | |
|---|---|---|---|---|
| 8.50 | ppm | s | 1 proton | NH |
| 8.15 | ppm | d | 1 proton | NH |
| 7.60–6.90 | ppm | m | 11 protons | ArH |
| 6.0 | ppm | d | 1 proton | COCHN |
| 4.65–4.20 | ppm | m | 1 proton | CH2 |
| 3.35–3.0 | ppm | m | 1 proton | CH2 |
| 3.0–2.60 | ppm | m | 2 protons | CH2 |
| 2.35 | ppm | s | 3 protons | CH3Ar |
| 2.30–1.50 | ppm | m | 2 protons | CH" |

IR: 3300, 2900, 1660, 1580, 1500, 1470, 1140, 820, 770, 750 cm$^{-1}$.

Example 29:
(5R,S)-N-(keto-4-phenyl-7-hexahydro-1,2,3,3a,4,5-pyrido[3,2,1-j,k]benzodiazepine[1,4]-yl-5)-N'-(bromo-4-phenyl-)-thiourea Formula (I): A=—(CH2)3—; R9=H; R10=methyl-4-phenyl; R11=H; R12=S; R13=NH; Ar=bromo-4-phenyl.

This product is obtained from 6.14 g (20 mmoles) of the amine obtained in Stage e of the preceding example and 4.28 g (20 mmoles) bromo-4-phenyl isothiocyanate, using the same procedure as in Example 10. The yield obtained is 4.2 g (45%) crystals. MP=185° C.
TLC: CH2Cl2/acetone 95/5 Rf=0.55.

| NMR: | | | | |
|---|---|---|---|---|
| 8.65 | ppm | s | 1 proton | NH |
| 8.15 | ppm | d | 1 proton | NH |
| 7.60–7.0 | ppm | m | 11 protons | ArH |
| 6.0 | ppm | d | 1 proton | COCHN |
| 4.65–4.20 | ppm | m | 1 proton | CH2 |
| 3.35–3.0 | ppm | m | 1 proton | CH2 |
| 3.0–2.70 | ppm | m | 2 protons | CH2 |
| 2.35 | ppm | s | 3 protons | CH3Ar |
| 2.30–1.60 | ppm | m | 2 protons | CH2 |

IR: 3300, 2900, 1660, 1600, 1580, 1510, 1480, 1380, 1160, 1060, 1000, 820, 745 cm$^{-1}$.

Example 30:
(5R,S)-N-(keto-4-phenyl-7-hexahydro-1,2,3,3a,4,5-pyrido[3,2,1-j,k]benzodiazepine[1,4]-yl-5)-N'-(ethoxycarbonyl-4-phenyl-)-urea Formula (I): A=—(CH2)3—; R9=H; R10=methyl-4-phenyl; R11=H; R12=O; R13=NH; Ar=ethoxy carbonyl-4-phenyl.

3.05 g (10 mmoles) of the previous amine (II) and 1.91 g (10 mmoles) ethoxycarbonyl-4-phenyl isocyanate are used, following the same procedure as in Example 10. The yield obtained in 1.5 g (30%) crystals.
MP>290° C.
TLC: CH2Cl2acetone 95/5 Rf=0.30.

| NMR: | | | | |
|---|---|---|---|---|
| 9.50 | ppm | s | 1 proton | NH |
| 8.0–7.10 | ppm | m | 12 protons | ArHNH |
| 5.3 | ppm | d | 1 proton | COCHN |
| 4.60–4.10 | ppm | m | 3 protons | OCH2, CH2N |
| 3.50–3.10 | ppm | m | 1 proton | CH2N |
| 3.10–2.60 | ppm | m | 2 protons | CH2 |
| 2.35 | ppm | s | 3 protons | CH3Ar |
| 2.40–1.60 | ppm | m | 2 protons | CH2 |
| 1.45–1.20 | ppm | t | 3 protons | CH3C |

IR: 3400, 2900, 1710, 1660, 1600, 1530, 1500, 1280, 1165, 1160, 1020, 830, 770 cm$^{-1}$.

Example 31:
(5R,S)-N-(keto-4-phenyl-7-hexahydro-1,2,3,3a,4,5-pyrido[3,2,1-j,k]benzodiazepine[1,4]-yl-4)-N'-(aminosulphonyl-4-phenyl-)-urea.

Formula (I): A=—(CH2)3—; R9=H; R10=methyl-4-phenyl; R11=H; R12=O; R13=NH; Ar=amino-sulphonyl-4-phenyl.

1.72 g sulphanilamide (10 mmoles) are dissolved in 25 ml dimethylformamide and 50 methylene chloride. 1.62 g (10 mmoles) N,N'-carbonyldiimidazole are added and the mixture allowed to stand for 4 hours at ambient temperature. After cooling to −5° C., 3.05 g (10 mmoles) amine (II) of the preceding examples are addd, dissolved in 50 ml methylene chloride. It is allowed to stand for 14 hours at ambneit temperature under constant stirring, then evaporated to dryness. The oily residue is redissolved with methylene chloride and washed with water. This yields an abundant precipitate which is washed with water and then dried. It is dissolved in methanol and absorbed on 50 g silica. This silica is placed at the top of a 250 g silica column which is eluted with ethylacetate-enriched methylene chloride. The yield obtained is 1.5 g (30%) crystals. MP=270° C.

TLC: CH2Cl2/AcOEt 50/50 Rf=0.60

| NMR: | | | | |
|---|---|---|---|---|
| 9.50 | ppm | s | 1 proton | NH |
| 7.85–7.0 | ppm | m | 12 protons | ArH, NH |
| 5.3 | ppm | d | 1 proton | COCHN |
| 4.60–4.15 | ppm | m | 1 proton | CH2N |
| 3.35 | ppm | s | 2 protons | SO2NH2 |
| 3.50–3.05 | ppm | m | 1 proton | CH2N |
| 3.05–2.60 | ppm | m | 2 protons | CH2 |
| 2.35 | ppm | s | 3 protons | CH3Ar |
| 2.60–1.50 | ppm | m | 2 prolons | CH2 |
| 1.45–1.20 | ppm | t | 3 protons | CH3C |

IR: 3300, 1660, 1570, 1540, 1480, 1340, 1150, 1100, 900, 820, 650, 540 cm$^{-1}$.

Toxicity and activity studies have been carried out on the compounds of the invention by "in vitro" and "in vivo" methods.

The acute toxicity, was examined by oral administration in the male mouse. The products were in this case administered in aqueous solution in a dose of 2 ml/100 g. The animals were then kept under observation for the three hours following administration, then daily for fourteen days, at which point they were sacrificed and underwent postmortem examination.

The LD$_{50}$ values (lethal doses causing death in 50% of the animals) were carried out by the method of Reed, J. L. and H. Muench (Am. J. Hyg., 1939 27 493). The LD$_{50}$ was found to be greater than 1000 mg/kg/$^{-1}$, indicating a low compound toxicity.

A. "In vitro" studies

The "in vitro" studies consisted in determining the binding affinity of the compounds of the invention for the cholecystokinin and gastrin receptors.

The aim of these experiments was to determine the solution concentrations of products of formula (I) which were capable of inhibiting in relation to the receptors in question fifty percent of the cholecystokinin bonds, labelled with iodine-121 (abbreviated below as [125I]-CCK8 sulphate) or in the case of the iodine-125-labelled gastrin receptor with the following receptors:

plasma membranes of the rat pancreas (male SD, rats, IFFA CREDO 200–225 g) (peripheral cholecystokinin receptor: CCK-A), guinea-pig brain membranes (males, COBLABO, 325–350 g) (central cholecystokinin receptor: CCK-B).

in accordance with the experimental protocol described by INNIS, R. B. and S. M. SNYDER, Eur. J. Pharmacol., 1980 65 123–124.

guinea-pig gastric glands (males, COB LABO, 325–350 g) in accordance with the method described by PRAISSMAN, M., M. E. WALDEN and C. PELLECHIA. Journal of Receptor Research, 1983 3 647–665 (gastrin receptor).

The results expressed as IC$_{50}$ or 50% inhibiting concentration are shown in Table I below. The unit of measurement is the nanomole.

TABLE I

| | Receptor bond | | |
|---|---|---|---|
| Example | CCK A nanomoles | CCK B nanomoles | Gastrin nanomoles |
| 1 | 59.6 | 431 | 14.4 |
| 2 | 1025 | 99.9 | 85.9 |
| 5 | 84.2 | 251 | 1.5 |
| 7 | 1726 | 255 | 40.5 |
| 8 | 3078 | 1808 | 60 |
| 10 | 3041 | 88 | 3.2 |
| 23 | 389 | 176 | 298 |
| 26 | >10000 | 137 | 36 |
| XXa | 1419 | 81.4 | 4.7 |

Examination of these results reveals that the products of the invention exhibit particularly promising selective affinities for the CCK B and/or gastrin receptors. Their selectivity may accordingly be:

either specific to the central receptors (CCK B) such as the compound of Example 2 which, in comparison with the compound of reference XXa, displays an activity of the same order on the CCK A and CCK B receptors but is 20 times less active on the gastrin receptors. This applies also to the compound of Example 23 which, although less active by a factor of 2 than the compound XXa on the CCK B receptor, is almost 60 times less active than this same reference compound on the gastrin receptor, so that it possesses an almost 30 times higher selectivity for the CCK B receptor;

or specific to the gastrin receptors such as the compounds of Examples 5 and 10 which have an activity similar to the reference compound XXa, but are respectively 3 and 1.5 times less active on the gastrin receptor.

In addition, the compounds of the invention exhibit an activity on the CCK B receptors as well as on the gastrin receptors, the selectivity of which is similar to or greater than that of compound XXa. The results obtained with the compound of Example 26 are shown by way of illustration:

| Selectivity: | | |
|---|---|---|
| GASTRIN/CCK A | XXa: | 1419/4.7 = 302 |
| | 26: | >10000/36 = >250 |
| CCK B/CCK A | XXa | 1419/81.4 = 17 |
| | 26: | >10000/137 = >70 |

B. "In vivo" studies

1. Gastrin-induced acid secretion

The activity of the products of the invention in relation to gastrin-induced acid secretion in the rat has been studied by the method described by Pascaud, X. P., A. R. Roger and M. J. H. Genton. Digestion, 177 16 57-68. The method consists in collecting the gastric acid secretion over two consecutive 2 hour periods in SD male rats (IFFA CREDO 250-300 g), provided with a chronic gastric fistula and continuously perfused i.v. with a pentagastrin solution (Peptavlon, ICI, 6 μg/kg/h). The inhibition of this secretion by the oral administration of 1 mg/kg product of the invention has been determined. According to this measurement technique, the compound of the invention of Example 10, which is a racemic compound, possesses an inhibiting activity identical with that of the enantiomer (XXa) of the prior art. The results are shown in Table II below.

2. Gastric evacuation

The antagonist activity of CCK on the digestive motor effects of the hormone has been examined in relation to the gastric evacuation, slowed down by the subcutaneous administration of CCK-8 (80 μg/kg) in SWISS male mice (IFFA CREDO 16-20 g), using the technique described by Lotti, V. J., D. J. Cerino, P. J. Kling and R. S. L. Chang. Life Sciences, 1986 39, 1631-1638. In this test, the stimulant effect of the products derives from their activity on the peripheral receptor CCK-A. The results obtained with the compound of Example 10 and the product (XXa) of the prior art are presented below (Table II) and expressed as their $ED_{50}$, which is the dose in mg/kg of test compound, administered orally, permitting a 50% inhibition of the slowing down of gastric evacuation induced by CCK-8 in the mouse.

| Compound | Gastric secretion % inhibition | Gastric evacuation $ED_{50}$ |
|---|---|---|
| (XXa) | 29% | 0.15 |
| Example 10 | 31% | 15.5 |

The results in Table II show that, administered orally in an equivalent dose (1 mg/kg), these two compounds are capable of inhibiting in significant fashion and with an identical intensity of action the stimulating effects of a submaximal gastrin dose on the gastric secretion. On the other hand, it required 100 times more of the product of Example 10 than of the product of the prior art (XXa) to obtain a 50% reduction in the inhibiting effects of CCK-8 on gastric evacuation, thus demonstrating the very low activity of the compound of the invention on the peripheral CCK-A receptors involved in this phenomenon. The compounds of the invention accordingly enable gastric secretion to be inhibited without inducing an increased gastric evacuation as a side effect. Expressed in more general terms, they act on the phenomena controlled by cholecystokinin B receptors or by the gastrin receptors without acting on the phenomena controlled by cholecystokinin A receptors as a side effect.

The products of the invention are administered in a form appropriate to the nature and severity of the condition for treatment. The daily dose in man is normally between 2 mg and 1 g product, which may be taken in one or more doses. The particular composition is prepared in a form compatible with the method of administration envisaged, for example tablets, dragees, capsules, suppositories, gels or suspensions. These compositions are prepared by methods normally known to the specialist and comprise 1-60 wt % active principle (compound of formula I) and 40-99 wt % of a pharmaceutical vehicle appropriate to and compatible with the active principle and the physical form of the envisaged composition. The method of preparation of tablets containing a compound of the invention is shown below by way of example.

PREPARATION OF TABLETS

| Active compound of Formula (I) | 1 to 75 mg |
|---|---|
| Lactose | 124 to 74 mg |
| Microcrystalline cellulose | 36 to 60 mg |
| Polyvinylpyrrolidone | 6 mg |
| Sodium carboxymethyl starch | 8 mg |
| Magnesium stearate | 1 mg |

Mix the active compound, lactose, microcrystalline cellulose and carboxymethyl starch.

Wet and granulate with an aqueous or alcoholic polyvinylpyrrolidone solution of suitable concentration.

Dry and calibrate the granular product.

Mix homogeneously the magnesium stearate.

Compress on a ratio of 200 mg per tablet.

We claim:

1. Benzodiazepines of Formula (I):

in which,
- R9 is hydrogen, nitro, halogen, cyano, trifluoromethyl, hydroxy, lower alkyl, lower alkowy, —COOR20, —N(R21)—R22;
- R10 is a phenyl, optionally mono- to tri-substituted by identical or different groups selected from among halogen, lower alkyl, lower alkoxy, cyano, nitro or trifluoromethyl;
- R11 is hydrogen or lower alkyl;
- R12 is an oxygen atom or a sulphur atom;
- R13 is a —N(R24)-group;
- R20 is hydrogen or lower alkyl;
- R21 and are identical or different and may be hydrogen or
- R22 an alkyl group;
- R24 is hydrogen or lower alkyl;
- Ar is an aromatic or heteraromatic hydrocarbon comprising one or two condensed rings, each of the rings comprising from 5 to 7 atoms including from 0 to 2 nitrogen heteroatoms; this aromatic or heteroaromatic being optionally mono- or di-substituted by identical or different groups selected from among lower alkyl, carboxyl, lower alkoxy carbonyl, sulphonyl, sulphamoyl, cyano, nitro, trifluoromethyl or, provided that R12 is sulphur, halogen or lower alkoxy groups:

A is [—CH(R1)—]a in which R1 is hydrogen or lower alkyl;

a is 2, 3 or 4;

e is 1 or 2.

2. Benzodiazepines according to claim 1, wherein R12 represents a sulphur atom.

3. Benzodiazepines according to claim 1, wherein the Ar group includes only one ring.

4. Benzodiazepines according to claim 2, wherein the Ar group includes only one ring.

5. Benzodiazepines according to claim 1, wherein the Ar group is a phenyl group substituted by a methyl group.

6. Benzodiazepines according to claim 2, wherein the Ar group is a phenyl group substituted by a methyl group.

7. Benzodiazepines according to claim 4, wherein the Ar group is a phenyl group substituted by a methyl group.

8. Benzodiazepines according to claim 2, wherein the Ar group is a phenyl group substituted by a methyl group or a bromine atom.

9. Benzodiazepines according to claim 3, wherein the Ar group is a phenyl group substituted by a methyl group or a bromine atom.

10. Benzodiazepines according to claim 1 wherein the A group is an ethylene (—CH2—CH2—) or trimethylene (—CH2—CH2—CH2—) bridge.

11. Benzodiazepines according to claim 2 wherein the A group is an ethylene (—CH2—CH2—) or trimethylene (—CH2—CH2—CH2—) bridge.

12. Benzodiazepines according to claim 5 wherein the A group is an ethylene (—CH2—CH2—) or trimethylene (—CH2—CH2—CH2—) bridge.

13. Benzodiazepines (—CH2—CH2—) according to claim 1 wherein the R9 group is a hydrogen atom or a chlorine atom in the para position in relation to the nitrogen atom shared with the diazepine ring and with the other nitrogen heteroring condensed with the diazepine ring, and in which e=1.

14. Benzodiazepines according to claim wherein the R10 group is a phenyl group, a phenyl group monosubstituted by a fluorine atom in the ortho position or by a methyl radical in the para position in relation to the carbon atom linking the phenyl ring with the diazepine ring.

15. Benzodiazepines according to claim 1 wherein the R11 group is a hydrogen atom.

16. Benzodiazepines according to claim 1 wherein the R13 group is a —NH— group.

17. Benzodiazepines according to claim 1 wherein the asymmetrical carbon atom of the benzodiazepine ring has an absolute configuration R in the nomenclature of Cahn, Ingold and Prelog.

18. Benzodiazepines according to claim 1 wherein the asymmetrical carbon atom of the benzodiazepine ring has an absolute configuration S in the nomenclature of Cahn, Ingold and Prelog.

19. A benzodiazepine of claim 1 which is (4R,S)—N—(keto-3-phenyl-6-tetrahydro-1,2,3,4-pyrrolo[3,2,1-j,k]-benzodiazepine-[1,4]-yl-4)-N'-(methyl-3-phenyl-)-urea and its isomer (5R).

20. A benzodiazepine of claim 1 which is (5R,S)—N—(keto-4-phenyl-7-hexahydro-1,2,3,3a,4,5-pyrido[3,2,1-j,k]-benzodiazepine-[1,4]-yl-5)-N'-(methyl-3-phenyl-)-urea and its isomer (5R).

21. A benzodiazepine of claim 1 which is (5R,S)—N—(keto-4-phenyl-7-hexahydro-1,2,3,3a,4,5-pyrido[3,2,1-j,k]-benzodiazepine-[1,4]-yl-5)-N'-(nitro-4-phenyl-)-urea, or 22. A benzodiazepine of claim 1 which is (5R,S)—N—(keto-4-phenyl-7-hexahydro-1,2,3,3a,4,5-pyrido[3,2,1-j,k]-benzodiazepine-[1,4]-yl-5)-N'-(bromo-4-phenyl0)-thiourea and its optical isomers and its isomer (5R).

* * * * *